United States Patent
Gordon

(10) Patent No.: US 9,420,873 B2
(45) Date of Patent: Aug. 23, 2016

(54) FLASH VORTEX BRUSH DEVICE AND METHOD

(76) Inventor: Jaimie David Gordon, Tacoma, WA (US)

(*) Notice: Subject to any disclaimer, the term of this patent is extended or adjusted under 35 U.S.C. 154(b) by 909 days.

(21) Appl. No.: 13/552,622

(22) Filed: Jul. 18, 2012

(65) Prior Publication Data

US 2013/0087171 A1  Apr. 11, 2013

Related U.S. Application Data

(60) Provisional application No. 61/627,308, filed on Oct. 11, 2011.

(51) Int. Cl.
| | |
|---|---|
| *B08B 3/04* | (2006.01) |
| *A46B 9/02* | (2006.01) |
| *B08B 9/04* | (2006.01) |
| *B08B 1/00* | (2006.01) |
| *B08B 3/02* | (2006.01) |
| *B08B 5/02* | (2006.01) |
| *A46B 11/06* | (2006.01) |
| *A46B 13/00* | (2006.01) |

(52) U.S. Cl.
CPC ... *A46B 9/02* (2013.01); *B08B 1/00* (2013.01); *B08B 3/02* (2013.01); *B08B 5/02* (2013.01); *B08B 9/04* (2013.01); *A46B 11/06* (2013.01); *A46B 13/006* (2013.01); *A46B 2200/3013* (2013.01)

(58) Field of Classification Search
CPC .. A46B 9/02; A46B 2200/3013; A46B 11/06; A46B 13/006; B08B 9/04; B08B 1/00; B08B 5/02; B08B 3/02
See application file for complete search history.

(56) References Cited

U.S. PATENT DOCUMENTS

| | | | | |
|---|---|---|---|---|
| 1,663,194 A | * | 3/1928 | Denman | E21B 37/02 15/104.2 |
| 1,700,364 A | * | 1/1929 | Bishop | B65D 35/285 222/102 |
| 2,517,017 A | * | 8/1950 | Nestle | E21B 37/00 15/104.2 |
| 4,490,872 A | * | 1/1985 | Drumm | A46B 5/00 15/182 |

(Continued)

OTHER PUBLICATIONS

Interstate 90 Connector Tunnel, Boston, Massachusetts, Jul. 10, 2006, National Transportation Safety Board, Accident Report, NTSB/HAR-07/02  PB2007-916203.  http://144.171.11.39/view.aspx?id=829017.

(Continued)

*Primary Examiner* — Alexander Markoff
(74) *Attorney, Agent, or Firm* — Patentpending, PLLC; Elizabeth Reilly

(57) ABSTRACT

Flash vortex brush cleaning apparatus is provided which comprises a device and method for cleaning inner channels of boreholes which have been drilled or cored within solid substrates, particularly, concrete, masonry, grout, where the boreholes are to be used to bond adhesive anchors therein. Flash vortex brush device comprises a straight tubular shaft; a coil cleaning brush. Tubular shaft includes a first end including an open inlet; opposing second end including an open outlet; first end including a connector element. Coil cleaning brush includes bristles secured in channel affixed wound proximate to second end of shaft developed of pitch to form an open wound coil. Connector element provides removable attaching means to a variety of pre-existing nozzles. For rapid efficient cleaning, first embodiment for use includes flash vortex brush removably attached with air nozzle; second embodiment for use includes flash vortex brush removably attached with water nozzle.

27 Claims, 8 Drawing Sheets

(56) References Cited

U.S. PATENT DOCUMENTS

| | | | | |
|---|---|---|---|---|
| 4,747,452 | A * | 5/1988 | Clark | E21B 37/02 15/104.12 |
| 5,402,548 | A * | 4/1995 | Adair | A46B 13/04 15/22.1 |
| 5,497,203 | A * | 3/1996 | Kayashima | H04N 5/144 348/451 |
| 5,829,521 | A * | 11/1998 | Brown, Jr. | E21B 37/02 15/104.2 |
| 5,947,203 | A * | 9/1999 | Brown, Jr. | E21B 37/02 15/104.2 |
| 6,209,647 | B1 * | 4/2001 | Brown, Jr. | E21B 37/02 15/104.2 |
| 6,401,813 | B1 * | 6/2002 | Carmichael | E21B 34/02 166/173 |
| 6,695,058 | B1 | 2/2004 | French | |
| 6,745,839 | B1 * | 6/2004 | Simpson | E21B 37/02 166/173 |
| 7,055,203 | B1 * | 6/2006 | Franzino | B08B 9/045 134/166 R |
| 7,543,354 | B2 | 6/2009 | Lee | |
| 7,712,520 | B1 | 5/2010 | Hettes | |
| 7,958,587 | B1 | 6/2011 | Hansen | |
| 8,186,092 | B2 | 5/2012 | Williams | |
| 2001/0042623 | A1 * | 11/2001 | Reynolds | E21B 37/045 166/312 |
| 2003/0102018 | A1 * | 6/2003 | Ostermeier | B08B 9/00 134/114 |
| 2007/0277345 | A1 * | 12/2007 | Spann | A47L 9/0673 15/395 |
| 2009/0217482 | A1 * | 9/2009 | Miyanaga | B08B 1/04 15/383 |
| 2009/0288682 | A1 * | 11/2009 | Glogger | B08B 1/00 134/8 |
| 2010/0065083 | A1 * | 3/2010 | Soetermans | A46B 15/0055 134/8 |

OTHER PUBLICATIONS

• *Moleculon Research Corp.* v. *CBS, Inc.*, 793 F.2d 1261, 229 USPQ 805 (Fed. Cir. 1986); In re Baxter, 656 F.2d 679, 686, 210 USPQ 795, 803 (CCPA 1981); *Ex parte* Davis, 80 USPQ 448, 450 (Bd. App. 1948). See MPEP 2111.03.
• Worchester Polytechnic Institute (WPI): "The Effects of Hole Cleaning on Post—Installed Anchor Systems in Concrete" by Keith Colemant; Cory Figlioni.

* cited by examiner

FIG. 7
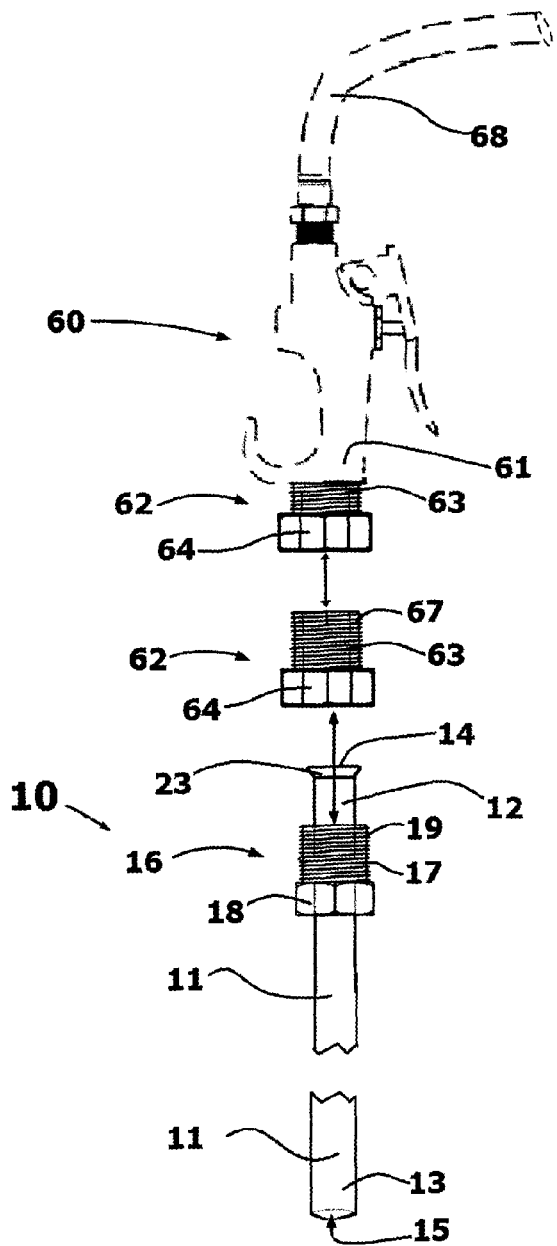
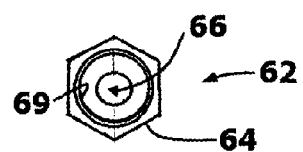
FIG.7A
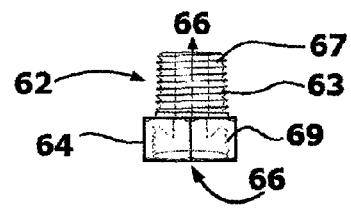
FIG. 7B

FLASH VORTEX BRUSH DEVICE AND METHOD

BACKGROUND OF THE INVENTION

1. Field of the Invention

The flash vortex brush apparatus relates to cleaning devices and more particularly to a rigid hollow tubular shaft comprising a coil cleaning brush apparatus for use with a pre-existing cleaning nozzle, for example, a pre-existing water nozzle of a type know in the art; or a pre-existing air nozzle of a type known in the art, the flash vortex brush device particularly efficient and effective in rapidly cleaning boreholes in solid substrates, for example, concrete boreholes, grout boreholes, masonry boreholes, and the like.

Problems exist in the current standard procedures for properly cleaning boreholes drilled in concrete, masonry, grout, and the like, that are intended to have various propriety anchors installed and bonded within them, according to anchor installation procedures of methods known in the art. Problems can include the longer amounts of time, money, and labor, it takes to clean boreholes under the standards and procedures currently used, and more importantly the dangerously inefficient and ineffective bonding of propriety anchors within boreholes due to second rate cleaning devices and methods currently used. Propriety anchors, such as anchors, wedge anchors, screwed in wedge anchors, driven anchors, adhesive anchors, anchor rods, bolts, dowels, steel bars, concrete reinforcing bars, threaded rods, threaded sleeve, reinforcing iron, bolts, dowels, steel bars, concrete reinforcing bars, are typical in such applications in the field. Anchors are typically bonded within the boreholes with various forms of epoxy, or catalyzed cements. Any failure of the anchor to bond within the borehole is unacceptable and can lead to fatal consequences, for example, the ceiling collapse in the Interstate 90 Connector Tunnel, Boston, Mass., Jul. 10, 2006, National Transportation Safety Board, ACCIDENT REPORT, NTSB/HAR-07/02 PB2007-916203. http://144.171.11.39/view.aspx?id=829017

On Jul. 10, 2006, a car occupied by a 46-year-old driver and his 38-year-old wife was traveling eastbound in the Interstate 90 connector tunnel in Boston, Mass., en route to Logan International Airport. As the car approached the end of the Interstate 90 connector tunnel, a section of the tunnel's suspended concrete ceiling became detached from the tunnel roof and fell onto the vehicle. Concrete panels from the ceiling crushed the right side of the vehicle roof as the car came to rest against the north wall of the tunnel. A total of about 26 tons of concrete and associated suspension hardware fell onto the vehicle and the roadway. The driver's wife, occupying the right-front seat, was fatally injured; the driver was able to escape with minor injuries. Major safety issues identified in this accident include insufficient understanding among designers and builders of the nature of adhesive anchoring systems; lack of standards for the testing of adhesive anchors in sustained tensile-load applications; inadequate regulatory requirements for tunnel inspections; and lack of national standards for the design of tunnel finishes. As a result of its investigation of this accident, the National Transportation Safety Board made safety recommendations to the Federal Highway Administration; the American Association of State Highway and Transportation Officials; the departments of transportation of the 50 States and the District of Columbia; the International Code Council; ICC Evaluation Service, Inc.; Powers Fasteners, Inc.; Sika Corporation; the American Concrete Institute the American Society of Civil Engineers; and the Asociated General Contractors of America.

Project documents attributed other test failures to insufficient curing time for the epoxy, holes that were drilled too deep, an inadequate amount of epoxy, and of importance here, holes that had not been properly cleaned. Epoxy Supplier's Recommended Procedures based relying on the second edition of the *Powers Rawl Fastening System Design Manual*, (PRFSDM) which was current at the time of the ceiling installation, addressed drilling and preparing anchor holes and using the product in cold weather. The PRFSDM, also, provided specific installation guidelines. For solid base materials, the (abridged) instructions are as follows:

Drill a hole to the size and embedment required.

Blow the hole clean with compressed air, brush the hole, and blow it clean again.

Reports revealed, in the case of the ceiling anchor bolts, the above stated method was used, such that the hole would be blown out with an air compressor, brushed out with a nylon brush, and blown clean again and further, revealed the bolts failed after the ceiling panels were installed. Examination of the one anchor that had been removed, indicated that the anchor bolt was improperly installed. Upon examining of the pulled-out anchor, it appeared to lack sufficient epoxy to fully fill the drilled hole. In addition to other major deficiencies cited in the report, there was a significant amount of concrete dust adhered to the epoxy surrounding the bolt, usually an indication that the drilled hole was not completely cleaned out prior to installation; and there was evidence that the drill hole was not brushed clear; and the anchor was not free of dirt, oil or foreign matter.

Therefore, it is known to create a borehole in a solid substrate, for example, cement, masonry, grout, by drilling a borehole extending from the exterior surface has vital problems. The borehole may become soiled with materials such as drilling mud residue "mud cake," fluid residue, and cement residue, adhering residues of the drilling dust, drilling mud, adhering fine-particle solids, which may substantially hamper subsequent down hole operations, and the satisfactory adherence of propriety anchors. In the drilling of boreholes in cement, cleaning steps must be introduced to ensure problem-free bonding of propriety anchors within the boreholes. To guarantee optimal bonding of the anchors, the borehole wall have to be freed from adhering residues of the drilling dust, drilling mud, adhering fine-particle solids, and dislodged residue. If this is not done, the layer of concrete is in danger of developing voids or channels which reduce the stability of the concrete.

In addition, residues of the drilling mud and the cement together can form a gelatinous mass which prevents the epoxy or catalyzed cements from setting so that the stability of the anchor bonded within the borehole is further reduced. In particular, all fine-particle solids still adhering to the wall of the borehole have to be removed to guarantee the performance of the epoxy or catalyzed cement. However, it becomes increasingly difficult to evacuate the debris and residue and detached debris, residue, scraped fine-particle solids, dust, out of the borehole in extended reach boreholes.

To that end, concrete inspectors typically inspect holes to determine their cleanliness prior to any anchor bonding therein. The cleaning process is regulated by the International Code Counsel which requires: (1) an Engineering Survey Report from the manufacturer of the anchor product for an approved process for installation of the specific anchor system; and (2) a licensed International Code Counsel Special Inspector be present during this process to verify compliance to manufacturer instructions. The current multi-step standard manufacturer procedure for cleaning holes drilled in concrete, masonry solid substrates for installation of propriety anchors is not fully accomplishing effective cleaning of boreholes. The typical procedure used in the field includes the method steps: Step 1. The hole is blown clean by a tube being inserted to the bottom of the borehole with air being blown through the tube to remove free standing drilling debris and residue. Step 2. The hole is manually brushed using a conical brush typically sold by the epoxy manufacturer. Step 3. The hole is blow out a second time by inserting the tube to the bottom of the drilled borehole. This standard procedure frequently yields minimal cleaning of the boreholes, leaving the drilled boreholes insufficiently cleaned and ill prepared to bond to propriety anchors therein. Several deficiencies in the current standard procedure include: use of an undersized brush; the amount of brushing actual performed is minimal; the flow of air is not sufficient to completely evacuate the drilling debris and residue. In other cases, the boreholes become damp creating the formation of a gel or paste formed from the concrete dust and debris which cannot be removed under the current standards including the velocity of air and size of brush. In the past, such concrete holes are cleaned by hand with a brush that is inserted into each hole. Obviously, this is a laborious, time consuming task. To add to the difficulty, holes are drilled into the concrete at particularly specific depths. Any cleaning must be certain of reaching the full depth of each hole, with the typically angled or conical borehole bottom surface, also, in need of being thoroughly cleaned.

Therefore, a number of devices and apparatuses have been developed to facilitate cleaning and removal of the residue, debris, incorporating brushes and other agitators, power tools. However, these devices and methods have been found to be unreliable or ineffective in the cleaning and the removing of material, residue, debris, dust, and the like from the borehole interior channel leading to improper anchor installation and attachment by epoxy or catalyst cements. These inefficiencies are costly to manufacturers, construction companies, and most importantly to human life. Therefore, there is a need for an improved apparatus and method to provide superior cleaning of boreholes which will be bonded to propriety anchors, including a borehole device and method to reach extended borehole depths.

2. Background Art of the Invention

A number of devices and apparatuses have been developed to facilitate cleaning and removal of the residue, debris, incorporating brushes and other agitators, power tools. However, these devices and methods have been found to be cumbersome, ineffective, time consuming, or costly, in removing the residue, debris, dust, and the like from the borehole interior channel. Prior patent references include U.S. Pat. No. 7,958,587 to Hansen describes a concrete hole brush apparatus including a tool and method for rapidly and effectively cleaning holes drilled in concrete. The apparatus comprises a conical brush attached to one end of a solid shaft; and the opposing end chucks into a variety of power drills, with the shaft size reduced to a chuck tip for best fit to those drills. The cylindrically brush sizes include ½ inch, ⅝ inch, ¾ inch, ⅞ inch, 1 inch, 1 1/⅛ inch, 1¼ inch.

U.S. Pat. No. 7,712,520 to Hetts describing a brush for a well bore casing comprising A brush for removing debris from a well bore casing, the brush comprising: a cylindrical base ring having front and rear edges, an outer surface, and adapted to be affixed to well tools; and a plurality of bristle assemblies circumscribing the outer surface of the base ring, each bristle assembly including a plurality of bristles, the bristles extending radially outward from the bristle assembly, the bristles of the bristle assemblies forming a brushing surface having a front face and a rear face; wherein a channel extends through the brushing surface from the front face to the rear face and having a depth extending radially inward from the brushing surface, the channel being substantially free of bristles; and wherein each bristle assembly includes an inner member having a channeled cross-section, and a retaining ring; and wherein each bristle has first and second ends, the bristles extending around the retaining ring so that a portion of each bristle is located between the inner member and the retaining ring, the retaining ring securing the bristles to the inner member at approximately their center, and wherein the ends of each bristle extend radially from the bristle assembly.

U.S. Pat. No. 7,543,354 to Lee describing a brush head for automatic dissolution vessel cleaner comprising a brush head for cleaning a vessel, comprising: a rotatable shaft defining a through passage, an upper end of said passage being couplable to a vacuum source; an inflow housing having at least one channel through which cleaning fluid is pumped, said shaft being rotatably mounted to said housing; and a brush assembly mounted on said shaft below said housing, a lower end of said passage being situated below said brush assembly, whereby when the brush head is inserted into the vessel, cleaning fluid is directed through said at least one channel into the vessel while said shaft rotates causing said brush assembly mounted thereon to rotate and clean an inner wall of the vessel with the fluid in the vessel being drawn into said passage via said lower end of said passage upon coupling of said upper end of said passage to the vacuum source.

Pat. Publication No. US2009/0288682 to Glogger describing a borehole cleaning device comprising a tubular shaft having a front opening with a shaft hollow space opening into the front opening, a region adjoining the front opening, a suction opening provided in an end region of the shaft opposite the region adjoining the front opening and a region adjacent to the suction opening and extending at an angle to the region of the shaft adjoining the front opening for forming a handle; and a plurality of brush members provided on the region of the shaft adjoining the front opening and extending radially outwardly.

PUBLICATIONS

Moleculon Research Corp. v. CBS, Inc., 793 F.2d 1261, 229 USPQ 805 (Fed. Cir. 1986); In re Baxter, 656 F.2d 679, 686, 210 USPQ 795, 803 (CCPA 1981); Ex parte Davis, 80 USPQ 448, 450 (Bd. App. 1948). See MPEP 2111.03.

Worchester Polytechnic Institute (WPI): "The Effects of Hole Cleaning on Post-Installed Anchor Systems in Concrete" by Keith Colemant; Cory Figlioni.

The flash vortex brush device and method of use provides an advantage over existing borehole cleaning devices and provides a remedy for hard to reach extended borehole bottom surfaces. The flash vortex brush device, in use, disclosed below provides a device and method for efficient and effective rapid cleaning of boreholes in use with easy attachment to cleaning nozzles, for example, a pre-existing air nozzle; a pre-existing water nozzle; and therefore provides for superior cleaned boreholes by the applied manual movement of the device in the channel of the borehole concomitant with the focused jet stream of air provided by the air-nozzle; or concomitant focused propulsion of water provided by the water-nozzle, accordingly, to ensure that the flash vortex brush device reaches the full lengths of each borehole, wherein the vortex created expels the debris, residue, and dislodged residue collected therein.

SUMMARY

In view of the background, and in accordance with the objects listed below it is therefore an object of the present invention to provide a borehole cleaning apparatus and method for rapidly and effectively cleaning boreholes drilled or cored in cement, masonry, or grout which cleans and removes adhering residues of debris, residue, mud, adhering fine-particle solids, rocks, stones for optimal bond of propriety anchors with the interior borehole concrete, masonry, or grout. In one embodiment, the flash vortex brush device when removably attached to a pre-existing water nozzle provides a device and method to clean boreholes which comprises combining two steps, currently practiced in cleaning boreholes, (1) the blowing step; and (2) the brushing step into one flash vortex brush device and method. In addition, the flash vortex brush device when removably attached to a pre-existing water nozzle provides a device and method to clean boreholes, more particularly wet boreholes, which comprises combining two steps, currently practiced in cleaning boreholes, (1) the blowing step, here, with water; and (2) the brushing step, into one flash vortex brush device and method. The unique specifications of the flash vortex brush removably attached to the pre-existing air nozzle provides the ideal water velocity that will achieve focused laminar or streamline flow exiting the open outlet of the tubular shaft and into the inner channel of the borehole because it provides the maximum debris and residue removal without eroding the borehole walls or floor. Thereby, both time and labor are decreased while borehole cleaning efficiency and effectiveness is increased. The flash vortex brush device and method can be adjusted to work with any propriety borehole size and type; and the flash vortex brush device and method can be adapted to be used with various cleaning nozzles.

In a second embodiment of the present invention, the flash vortex brush device provides a device and method of cleaning a borehole comprising a flash vortex brush device and method comprising the dual cleaning action of a coil cleaning brush coupled with the contemporaneous action of a pressurized laminar or streamlined jet-stream of compressed air provided by a pre-existing air nozzle attached to air source, the flash vortex brush device when removably attached to a pre-existing water nozzle provides a device and method to clean boreholes which comprises combining two steps, currently practiced in cleaning boreholes, (1) the blowing step; and (2) the brushing step into one flash vortex brush device and method. In addition, the flash vortex brush device when removably attached to a pre-existing water nozzle provides a device and method to clean boreholes, more particularly dry boreholes, which comprises combining two steps, currently practiced in cleaning boreholes, (1) the blowing step, here, with air; and (2) the brushing step, into one flash vortex brush device and method. The unique specifications of the flash vortex brush removably attached to the pre-existing air nozzle provides the ideal air velocity that will achieve focused laminar or streamline flow exiting the open outlet of the tubular shaft and into the inner channel of the borehole because it provides the maximum debris and residue removal without eroding the borehole walls or floor. Accordingly, both time and labor are decreased while borehole cleaning efficiency and effectiveness is increased. The flash vortex brush device and method can be adjusted to work with any propriety borehole size and type; and the flash vortex brush device and method can be adapted to be used with various cleaning nozzles.

In a third embodiment, the flash vortex brush device and method of use provides a device and method of cleaning a borehole comprising a flash vortex brush device coupled to a water nozzle where the water nozzle is coupled to a fluid including agents, solvents, or disinfectants; or any desired fluids including a variety of agents, to provide the ideal fluid velocity that will achieve laminar or streamline flow because it provides the maximum debris and residue removal without eroding the borehole walls or floor.

Propriety anchors may include anchors, wedge anchors, driven anchors, screwed in wedge anchors, anchor rods, threaded rods, threaded sleeve, reinforcing iron, bolts, dowels, steel bars, concrete reinforcing bars, ceiling anchor bolts, and the like, as mentioned above. The flash vortex brush cleaning apparatus is provided by the present invention which comprises a device and method for rapid and efficient cleaning of boreholes which have been drilled or cored within solid substrates, particularly, concrete, masonry, grout, where the boreholes are used to anchor propriety anchors which must be bonded with structural epoxies or catalyst cements. The flash vortex brush device in use is coupled to a pre-existing cleaning nozzle and connecting pressure source. The flash vortex brush comprises a hollow straight tubular shaft; and a coil cleaning brush. The hollow tubular shaft defines a through passage, and the tubular shaft includes a first flared end including a defined open inlet and opposing second non-flared end including a defined open outlet joined by at least approximately 12 inches of tubular shaft therebetween. The connector element is positioned proximate to the first flared end of the tubular shaft such that it is available to removably attach with a variety of other connection elements. The coil cleaning brush includes a plurality of bristles secured in a holding channel affixed wound proximate to the second end of the tubular shaft to form an open wound coil brush face having a length extending less than half the length of the tubular shaft, having a substantial helical shape and as so a generally helical keyway path having no bristles, also, is formed, therein, for the flow of water and residue; and for air and residue, dependent upon the cleaning nozzle used.

The connector element positioned upon the tubular shaft acts to removably attach to a variety of connection elements, for example, a pre-existing connection element of pre-existing cleaning nozzles, pre-existing couplers, pre-existing unions providing versatility to the flash vortex brush device. A first embodiment for use with the flash vortex brush device includes the flash vortex brush device, with the inclusion of coupling means, removably attached with a pre-existing connection portion of a pre-existing water nozzle removably attached to water source; a second embodiment for use with the flash vortex brush device includes flash vortex brush device, with the inclusion of coupling means, removably attached to a pre-existing connection portion of a pre-existing air nozzle attached to an air source.

The residue material in the borehole may be mud residue, such as mud-cake, dust, debris, cement debris, drilling dust, adhering fine-particle solids, adhering-solid particles, small rocks, stones, residues, and the like, produced by the operations involved in creating, particularly, a concrete borehole. Further, the material may be sand, dust, or scale which, may build up in the borehole drilling production. The material may have been adhered to the inner wall of the borehole, and may be descaled and dislodged from the borehole inner wall in the course of the cleaning operation. Thus, the borehole is cleaned by the flash vortex brush, according to the present invention, in one embodiment, such that the borehole is cleaned by the flash vortex brush such that the residue is dislodged and evacuated from the interior of the borehole by the dual action of the coil cleaning brush and the impelled jet stream of water when a pre-existing water nozzle, attached to a pre-existing water source, is coupled to the flash vortex brush, and subsequently the flash vortex brush is inserted into the borehole channel to be cleaned. Thus, the flash vortex brush device is capable of reaching extended depths contacting the walls of the borehole and the typically angled or conical bottom floor surface of the borehole channel to ensure superior cleaning to the interior bottom surface of the borehole channel such that the residue is dislodged and evacuated from the interior of the borehole by the dual action of the coil cleaning brush and the impelled laminar jet stream of water when a pre-existing water nozzle is removably attached to the flash vortex brush. Therefore, the flash vortex brush provides for optimal bond of anchors with the cement of the borehole.

The same is true, when, in use, the flash vortex device is removably attached to a pre-existing air nozzle, attached to an air supply, Thus, the borehole is cleaned by the flash vortex brush, according to the present invention, such that the residue is dislodged and evacuated from the interior of the borehole by the dual action of the coil cleaning brush and the impelled laminar jet stream of air when a pre-existing air nozzle, attached to a pre-existing air source, is removably attached to the flash vortex brush and the flash vortex brush is subsequently inserted into the channel of the borehole to be cleaned. Thus, the flash vortex brush device is capable of reaching extended depths contacting the walls of the borehole and the typically angled or conical bottom floor surface of the borehole channel to ensure superior cleaning to the interior bottom surface of the borehole channel such that the residue is dislodged and evacuated from the interior of the borehole by the dual action of the coil cleaning brush and the impelled laminar jet stream of air when a pre existing air nozzle is coupled to the flash vortex brush. Therefore, the flash vortex brush provides for optimal bond of anchors with the cement of the borehole.

As mentioned above, the flash vortex brush device comprises a straight hollow tubular shaft defining a through passage including a connector element thereon; and a coil cleaning brush. The straight tubular shaft comprises a first end and a second end; first end includes a first defined open inlet to receive the water source; or to receive the air source, depending upon the cleaning nozzle used; and second end includes an opposing second defined open outlet to provide a means through which to deliver the focused laminar jet stream of water; or focused laminar jet stream of compressed air. The tubular shaft can be at least 12.00 inches in length of the straight shaft. The external diameter of the tubular shaft is of a first diameter and the internal diameter of the shaft is of a second diameter. The flash vortex brush is permanently affixed proximate to the second end of the straight shaft, and is wound convoluting upon the tubular shaft in a helical coil having the appropriate convolutions of pitch to yield a helical brush face having at least 5 coils having a brush face length convoluting from the second end of the tubular shaft towards the second end of the tubular shaft, a length less than one half the length of the tubular shaft; and has a plurality of bristles arranged and sized to a diameter less than the inner diameter of the borehole to be cleaned. More particularly, flash vortex tubular shafts may be provided in 12 inches; 18 inches; or any desired or needed length; and flash vortex coil cleaning brushes may be provided with outer diameters range from approximately ⅝ inch to approximately 3.00 inches but not limited to, while coil cleaning brush face lengths range from approximately 4.00 inches to approximately 6.00 inches. The coil cleaning brush has convolutions of pitch to facilitate moving loose product or debris to one side, or to annulus spaces within the borehole channel, and through the generally helical keyway path created therein; and has a plurality of bristles arranged and sized to a diameter equal to or slightly greater than the inner diameter of the borehole to be cleaned so as to contact the borehole walls at all points along the coil cleaning brush face; and at the same time allow debris to exit up through the annulus to the internal walls of the borehole and through the keyway path having no bristles created therein the coil cleaning brush. The coil brushes can have left or right hand lead.

The coil cleaning brush is bound on one side longitudinally with a malleable metal flat back holding channel which provides a holding means for the bristles and provides an attaching means to permanently affix the coil cleaning brush to the tubular shaft. The flat back channel includes a substantially U-shaped channel including two vertically aligned side walls joined by a horizontally aligned base; the U-shaped channel has an exterior surface and interior surface. The metal holding channel can be manufactured using metal, steel, stainless steel, brass, plastic, polymeric substrates. The coil cleaning brush can be mounted permanently to the tubular shaft with the use of thin layer of fluid adhesives, for example, JB Weld, or can be permanently affixed by the use of clips, J-bolts, tapered locking collars, flanges, compression, or welded, and the like and applied to the exterior surface of the base of the channel and attached proximate to the second non-flared end of the tubular shaft in the configured pitch and spacing, as described above. In another embodiment, the coil brush sleeve may be configured such that the bristles are secured in the "U" shaped channel by means including a retaining wire which may be used to abet in anchoring the channel of bristles coiled to the tubular shaft. The tubular shaft onto which the coil cleaning brush will be mounted can be made of rigid metal, of steel, stainless steel, copper, steel, platinum, radium, polyvinyl chloride or other durable materials suitable for the applications provided by the present invention. The coil cleaning brush includes bristles that may be manufactured from nylon, stiff nylon, multiple polymer designations including 6.6, 6.10, 6.12 heat stabilized abrasive impregnated, metal detectable, static control and conductive, polyester, polypropylene, PTFE (Teflon); wire including stainless steel, carbon steel, bronze, brass; animal hair including but not limited to horsehair, hog bristle, goat hair, camel hair, sable hair; vegetable fibers including Tampico, Palmyra, Bassine, Union Fiber, African Bass, and include anti static capability. The coil cleaning brush can be provided by a pre-formed coil cleaning brush sleeve. The coil cleaning brush sleeve, as such, is coiled having an internal diameter less than the external diameter of the tubular shaft to provide a snug fit when mounted coiled around and removably affixed to the external surface of the tubular shaft.

The first flared end of the straight tubular shaft includes a connector element positioned thereon, to provide an attachment means which can be removably attached to a pre-existing connection element of a pre-existing cleaning nozzle, more particularly, a pre-existing water nozzle; or in another embodiment a pre-existing connection element of a pre-existing air nozzle, as known to those in the art. In another embodiment, the flash vortex brush can be removably attached to the pre-existing connection element of the pre-existing water nozzle with the inclusion of coupling means positioned between the connector element upon the tubular shaft and the pre-existing connection element of the pre-existing water nozzle. Accordingly, a pre-existing air nozzle can be removably attached to the first end of the tubular shaft by means of coupling means with the flash vortex brush and a pre-existing connection element of an air nozzle.

Also, disclosed is a method for cleaning debris, adhering residues of the drilling dust, drilling mud, adhering fine-particle solids, rocks, and stones from an inner channel diameter and wall of a concrete borehole using the flash vortex brush. In a first exemplary embodiment, the flash vortex brush device is used with a pre-existing water nozzle. The method includes the steps of providing an open concrete borehole having an inner channel diameter and surrounding walls which has residue adhered or collected thereon. The method for cleaning includes providing a flash vortex brush device comprising a straight tubular shaft defining a through passage, a connector element positioned thereon the tubular shaft, and a coil brush; the length of the straight tubular shaft sufficient to reach the bottom of the selected borehole and the coil cleaning brush having an outside diameter equal to or slightly less than the borehole. The tubular shaft has a first end and a second end; the first end includes a first defined open inlet and the second end includes a second defined open outlet joined by at least 12 inches of tubular shaft therebetween; the coil cleaning brush mounted in an open wound coil having a brush face substantial helical in form wound proximate to the second end of the tubular shaft.

The method for cleaning further includes providing a pre-existing water nozzle and pre-existing coupling means, for example, threaded reducer bushing; and modified standard hose cap. The threaded reducer bushing is configured to threadably removably attach on one end to the modified standard hose cap, and on the opposing end to threadably removably attach to the threaded connector element, for example, a flare nut, positioned proximate to the first flared end upon the tubular shaft of the flash vortex brush device. Any connecting means, known in the art, may be used which includes a through space with locking means to removably attach the flash vortex brush to the pre-existing water nozzle. The modified hose cap, in turn, is removably attached to the pre-existing connection element of the pre-existing water nozzle.

The defined open inlet of the flash vortex brush device provides a means for receiving pressurized water from the water nozzle attached to water source into the tubular shaft to be blown and propelled and circulated in the inner channel of the borehole. The pressurized water is exited through the defined open outlet of the flash vortex brush device where a focused laminar jet-stream of water is powerfully blown impelled into the channel of the borehole able to reach and contact the borehole wall and typically angled or conical bottom surfaces so that debris and residue is dislodged, and further blowing of the powerful focused laminar jet-stream of water contemporaneous with the brushing movement of the flash vortex brush provides a powerful vortex and therewith propels air entrained with debris, residue, detached small-particles, dust, to be driven back up into the annulus and keyway path within the coil cleaning brush carrying and retaining borehole debris and residue with the water, and finally the water including retained debris and residue is expelled out of the borehole opening into the environment.

The flash vortex brush device is ready to use in the next step of the method of cleaning. By way of example, a cement borehole is described in use with the flash vortex brush. The operator cleans the selected cement borehole by inserting the flash vortex brush "in and out" of the channel of the cement borehole leading with the first end of the tubular shaft with coiled brush securely attached; and moving the flash vortex brush device through the length of the interior channel of the borehole such that the plurality of bristles or filaments of the coiled brush contacts the interior cement wall scraping the adhering residues, debris, dust, mud, adhering fine-particle solids, rocks, stones and contemporaneous air nozzle impelling a jet stream of water pumped under pressure downwards through the hollow tubular shaft to emerge through the bottom at the second defined open end of the shaft to the bottom of the borehole where the contemporaneous movement of the coil cleaning brush causes a vortex of air and deposits, debris, detached fine-particle solids, rocks, stones, dust, residue thus scraped to be forced upwards through the annulus space between the shaft and the borehole walls and, therefore, deposits are transported from the borehole with the pressurized water. Next step in the cleaning method includes the operator drawing the flash vortex brush out of the cement borehole. The next step requires the operator to repeat the above described steps of inserting the flash vortex brush into the borehole, brushing the flash vortex brush within the borehole contemporaneous with the projection of the jet-stream of water followed by drawing the flash vortex brush device out of the borehole. The steps of inserting the flash vortex brush device, brushing with the flash vortex brush and the contemporaneous blowing of water into the channel of the borehole, and the drawing out of the flash vortex brush device is repeated over again, and again, until the borehole is thoroughly cleaned. Thus, a drilled concrete, masonry, grout, borehole is efficiently, effectively, and rapidly cleaned.

The pre-existing water nozzle can easily be removed and a pre-existing air nozzle attached to an air source can be threadably coupled to the flash vortex brush device via a coupling means, for example, a threaded reducer bushing.

The method for cleaning further includes providing a pre-existing air nozzle and pre-existing coupling means, for example, threaded reducer bushing configured to threadably removably attach on one end to the air nozzle device and on the opposing end to threadably removably attach to the threaded connector element, for example, a flare nut, positioned proximate to the first flared end upon the tubular shaft of the flash vortex brush device. Any connecting means, known in the art, may be used which includes a through space with locking means to removably attach the flash vortex brush to the pre-existing air nozzle. The defined open inlet of the flash vortex brush device provides a means for receiving compressed air from the air nozzle attached to air source into the tubular shaft to be blown and propelled and circulated in the borehole. The compressed air is exited through the defined open outlet of the flash vortex brush device where a focused laminar jet-stream air is powerfully blown impelled into the channel of the borehole able to reach and contact the borehole wall and typically angled or conical bottom surfaces so that debris and residue is dislodged, and further blowing of the powerful focused laminar jet-stream of air contemporaneous with the brushing movement of the flash vortex brush provides a powerful vortex and therewith propels air entrained with debris, residue, detached small-particles, dust, to be driven back up into the annulus and keyway path within the coil cleaning brush carrying and retaining borehole debris and residue with the air, and finally the air including retained debris and residue is expelled out of the borehole opening into the environment.

The flash vortex brush device is ready to use in the next step of the method of cleaning. By way of example, a cement borehole is described in use with the flash vortex brush. The operator cleans the selected cement borehole by inserting the flash vortex brush "in and out" of the channel of the cement borehole leading with the first end of the tubular shaft with coiled brush securely attached; and moving the flash vortex brush device through the length of the interior channel of the borehole such that the plurality of bristles or filaments of the coiled brush contacts the interior cement wall scraping the adhering residues, debris, dust, mud, adhering fine-particle solids, rocks, stones and contemporaneous air nozzle impelling a jet stream of air pumped under pressure downwards through the hollow tubular shaft to emerge through the bottom at the second defined open end of the shaft to the bottom of the borehole where the contemporaneous movement of the coil cleaning brush causes a vortex of air and deposits, debris, detached fine particle solids, rocks, stones, dust, residue thus scraped to be forced upwards through the annulus space between the shaft and the borehole walls and, therefore, deposits are transported from the borehole with the pressurized air. Next step in the cleaning method includes the operator drawing the flash vortex brush out of the cement borehole. The next step requires the operator to repeat the above described steps of inserting the flash vortex brush into the borehole, moving the flash vortex brush within the borehole contemporaneous with the projection of the jet-stream of air from the air followed by drawing the flash vortex brush device out of the borehole. The steps of inserting the flash vortex brush device, moving the flash vortex brush, and the drawing out of the flash vortex brush device is repeated over again, and again, until the borehole is thoroughly cleaned. Thus, a drilled concrete, masonry, grout, borehole is efficiently, effectively, and rapidly cleaned.

Conventionally, a cleaned concrete to determine if the concrete borehole is properly cleaned when upon follow inspection, a licensed inspector using an air nozzle; and air nozzle affixed to a hollow straight tubular shaft at least 12 inches without a coiled brush is inserted into the newly cleaned cement borehole channel such that when a jet-stream of air is propelled down into the channel reaching the bottom of the borehole, no visible dust or fine-particle solids, or residue exits the newly cleaned concrete borehole. Upon follow up inspection of a cleaned borehole, field testing of the flash vortex device and method exhibited a superior cleaned borehole. Therefore, the flash vortex brush provides for rapid, efficient cleaning and for optimal bond of anchors with the cement of the borehole.

Accordingly, the problem addressed by the present invention, was achieved to provide a flash vortex brush and method that rapidly and efficiently cleans boreholes which removes and evacuates debris, drilling mud, adhering fine-particle solids, rocks, stones, from the inner channel of the borehole to provide a clean borehole for optimum bonding of epoxy or catalyst cements where priority anchors are to be affixed.

The flash vortex brush apparatus, according to the present invention, provides a device and method to resolve major safety issues identified with cleaning boreholes particularly in the nature of insufficient devices and methods among designers, contractors, manufacturers, and builders currently applied in cleaning boreholes to which adhesive anchoring systems will be bonded therein; lack of methods for the testing of cleaned boreholes to which adhesive anchoring systems will be bonded therein; and lack of state and national standards for devices and methods of cleaning boreholes among the National Transportation Safety Board; Federal Highway Administration; the American Association of State Highway and Transportation Officials; the departments of transportation of the 50 States and the District of Columbia; the International Code Council (ICC); ICC Evaluation Service, Inc.; Powers Fasteners, Inc.; Sika Corporation; the American Concrete Institute; the American Society of Civil Engineers; and the Associated General Contractors of America.

As the flash vortex brush device and method provides the needed ability to thoroughly clean boreholes drilled in concrete, grout, masonry materials without constant supervision, it is anticipated, here by the present invention, that in time all engineers, and other design authorities, would require the flash vortex brush device and practice of method, for all post-installed propriety anchor systems. Under current practices, full time inspection of post-installed propriety anchor systems is required by the International Building Code/International Code Council (IBC/ICC). Consistent use of the flash vortex brush device and method, according to the present invention, on construction projects, may allow the governing code authorities to reduce the current requirement of full-time inspection to part-time inspection for propriety anchor systems ensuing savings of momentous amounts of money in inspection fees charged each year.

Still further, Government, or Military personnel need to be able to clean cement, masonry, or grout boreholes in the field to ensure that boreholes rapidly and efficiently removes and evacuates debris and residue from the borehole to provide a clean conduit for epoxied anchors to adhere. Government, or Military personnel may not be able to return to a construction sites where boreholes intended for propriety anchors to be bonded therein, in the near future so a secure structure having secure anchors is vital. Therefore, there is a need for Government, or Military personnel, for a flash vortex brush that provides for rapid, efficient, effective, and reliable superior cleaning of boreholes which is convenient to use, easy to replace, economic to manufacture, and readily usable with various pre-existing nozzles.

Therefore, a need exists for a borehole flash vortex brush device that efficiently removes and evacuates debris, drilling dust, adhering fine-particle solids, and residues from inner channels of boreholes; and provides increased removal of said debris; to guarantee effective bonding of propriety anchors within the borehole channel; and further there is a need for a flash vortex brush device that is easy to replace, versatile, and holds up to the conditions inside the channel of the borehole.

The general purpose of the flash vortex brush apparatus and method, described subsequently in greater detail, is to provide a flash vortex brush device and method which has novel features that result in an improved borehole cleaning apparatus and method which is not anticipated, rendered obvious, suggested, or even implied by prior art, either alone or in combination thereof. To attain this, the flash vortex brush provides a device for rapidly and effectively cleaning holes drilled in solid substrates, for example, concrete, masonry, grout, limestone, marble, but not limited to. As noted, the boreholes are used in anchoring various propriety anchors, such as anchors, wedge anchors, screwed in wedge anchors, adhesive anchors, anchor rods, bolts, dowels, steel bars, concrete reinforcing bars, threaded rods, threaded sleeve, reinforcing iron, bolts, dowels, steel bars, concrete reinforcing bars, are typical in such applications in the field, that must be bonded within the holes. The boreholes must be clean of all residues of the drilling dust, adhering fine-particle solids, adhering-solid particles, small rocks, stones, and residues and cleaned of detached debris and residues collected on the borehole bottom surfaces so that the propriety anchors are able to effectively and reliably bond with the borehole inner surfaces. The present flash vortex brush device is provided having a hollow rigid tubular shaft; connector element; unique coil cleaning brush including plurality of coil cleaning brush sizes to provide for increased cleaning of boreholes which operationally include a variety of sizes.

The flash vortex brush, in use, removably attaches into selected cleaning nozzles, for example, a pre-existing water nozzle of a type known in the art; or a pre-existing air nozzle of a type known in the art. The brushing action of the flash vortex brush device concomitant with the blowing of laminar focused jet stream of water and applied method steps ensures that an operator reaches the entire borehole depth, borehole bottom surface, and side walls to guarantee rapid, superior, reliable cleanliness. Accordingly, the brushing action of the flash vortex brush device concomitant with the blowing of laminar focused jet stream of air and applied method steps ensures that an operator reaches the entire borehole depth, borehole bottom surface, and side walls to guarantee rapid, superior, reliable cleanliness Also, the use of the extension shaft ensures that an operator penetrates to the entire borehole depth to guarantee cleanliness in boreholes having extended depths.

Thus has been broadly outlined the more important features of the flash vortex brush device and method so that the detailed description of the present invention described below may be better understood and to the end that the present contribution to the art may be better appreciated.

It is an object of the present invention to provide a flash vortex cleaning device and method by using this unique novel device which combines two steps into one device, blowing step and the brushing step, such that the cleaning step and the blowing step are performed contemporaneously to provide the debris left from the coring or drilling process to be substantially completely evacuated from the concrete borehole in one easy step, taking from 5 to 10 seconds in holes 1½ inches and smaller, using minimally amounts of water.

It is an object of the present invention to provide a flash vortex cleaning apparatus and method for easy use with a variety of pre-existing cleaning nozzles, for example, pre-existing water nozzle; pre-existing air nozzle.

It is an object of the present invention to provide a flash vortex brush apparatus and method which provides a vertical brushing action contemporaneously applied with a powerful laminar focused jet stream of compressed air for rapid and efficient cleaning of boreholes including boreholes with extended lengths.

It is an object of the present invention to provide a flash vortex brush device and method which provides brushing action contemporaneously applied with a powerful laminar focused jet stream of pressurized water which provides blowing action in one step to provide rapid and efficient cleaning of boreholes.

It is an object of the present invention to provide a flash vortex brush device and method to provide optimal cleaning and substantially complete removal of borehole debris, residue, and detached residue from drilled or cored boreholes in solid substrates, including boreholes having extended depths to ensure superior borehole cleaning.

It is an object of the present invention to provide a flash vortex brush device and method to include a tubular shaft extension when needed for cleaning boreholes having extended depths.

It is an object of the present invention to provide a flash vortex brush device and method to save time in cleaning concrete boreholes by eliminating tandem steps used in current cleaning borehole procedures.

It is an object of the present invention to provide a flash vortex brush device and method to provide a standard device and method steps when in use provides for superior and reliable cleaning of boreholes intended to be bonded with priority anchors and further to ensure bonding agent adhesion.

It is an object of the present invention to provide a flash vortex brush device and method to provide superior cleaning of boreholes to provide maximum bonding of propriety anchors such that the anchor pull strength is approximately doubled.

It is an object of the present invention to provide a flash vortex brush device and method to provide superior cleaning of boreholes in approximately less than one quarter of the time it takes to clean boreholes under the currently practiced standards, therefore, saving money, time, and labor costs.

It is an object of the present invention to provide a flash vortex brush device and method to be able to negate problems in concrete, masonry, granite, and the like, borehole inspections by a concrete inspector.

Still further, it is an object of the present invention to provide a flash vortex brush apparatus and method to provide a standard device and method steps when in use provides for superior and reliable cleaning of boreholes intended to be bonded with priority anchors to be adopted by the National Transportation Safety Board makes safety recommendations to the Federal Highway Administration; the American Association of State Highway and Transportation Officials; the departments of transportation of the 50 States and the District of Columbia; the International Code Council; ICC Evaluation Service, Inc.; Powers Fasteners, Inc.; Sika Corporation; the American Concrete Institute; the American Society of Civil Engineers: and the Associated General Contractors of America.

Still another object of the flash vortex brush device and method is to provide a plurality of coil cleaning brush sizes for cleaning a plurality of drilled or cored borehole sizes.

Still another object of the flash vortex brush device is to provide a borehole cleaning device that can be economically produced and maintained.

The flash vortex brush device and method provides superior cleaning of drilled or cored boreholes in concrete, masonry, granite, and the like. The present invention, in use, provides increased cleaning of material, adhered residues of the drilling dust, debris, adhering fine-particle solids, adhering-solid particles, small rocks, loosened materials, and the like, and the removal of same from the channel of the borehole. In addition, the flash vortex brush removably attached to a cleaning nozzle, for example, a pre-existing water nozzle; pre-existing air-nozzle, is capable to deliver a high velocity of air or water contacting the hard to reach conical or angled bottom surface of the borehole and sidewalls of the inner channel of the borehole to be cleaned; and decreases the time necessary to effectively clean the boreholes, Field testing has proven the effectiveness of the flash vortex brush and method; testimonial by this inventor a licensed ICC Special Inspector and Washington Association of Building Officials, Licensed Special Inspector for propriety anchor installation. After arriving, at a job site, a contractor informed the Special Inspector (who was there for inspection of the installation of over 400 all thread anchors into new concrete stem walls using an engineer approved structural epoxy as required by the ICC,) that all of the holes had been cleaned on the previous day and that it had taken most of the day to accomplish the manufacturer required process. To verify the cleanliness of the drilled holes in concrete the Special Inspector provided the flash vortex brush to the contractor for use with the present method. The contractor connected the flash vortex brush to a pre-existing air nozzle and an air source producing 80 to 120 psi of air flow and inserted the flash vortex brush device, of the present invention, into the previously cleaned 8 inches deep hole while releasing air from the pre-existing air nozzle. A large cloud of dust and debris began to exit the hole as if it had not been previously cleaned. The contractor then asked permission to use the flash vortex brush to re-clean all 400 of the holes in the concrete stem wall so that the epoxy and all thread anchors could be placed in holes that were truly clean. The cleaning was completed in less than 2 hours. The laborer who used the flash vortex brush was "covered" in concrete dust. Because of the effectiveness of the flash vortex brush and the drastic reduction in time required to accomplish the process, the contractor wanted to acquire a supply of the novel invention for further use on his current project and ones in the future. Clearly, there is a need in the trade, for the flash vortex brush to provide a means to efficiently, economically, and successfully clean deep holes drilled in concrete or masonry to enable secure positioning and installation of all propriety anchor systems associated with said holes filled with structural epoxy, grout, wedge anchors and driven anchors. The new and improved flash vortex brush device and method provides a propriety procedure for cleaning boreholes in preparation for installation of epoxy anchors which may reduce special inspection from full time to periodic. As such, the present invention, as disclosed, has the potential to save millions of dollars in special inspection fees.

Further features and advantages of the present invention will become apparent to those of ordinary skill in the art in view of the detailed description of preferred embodiments below, when considered together with the appended claims.

BRIEF DESCRIPTION OF THE DRAWINGS

The novel features that are characteristic of the preferred embodiment of the invention are set forth with particularity in the claims. The invention itself may be best understood, with respect to its device and method of use, with reference to the following description taken in connection with the accompanying drawings in which:

FIGS. 2, 3 and 3A are explanatory drawings showing details of the flash vortex brush device as shown in FIG. 1, wherein FIG. 3A is a cut-out view of the coil cleaning brush.

FIGS. 5, 5A and 5B are explanatory drawings showing details of the flash vortex brush device in use with a pre-existing water nozzle, as shown in FIG. 4.

FIGS. 7, 7A and 7B are explanatory drawings showing details of the flash vortex brush device in use with a pre-existing air nozzle, as shown in FIG. 6.

Figures 1, 1A:
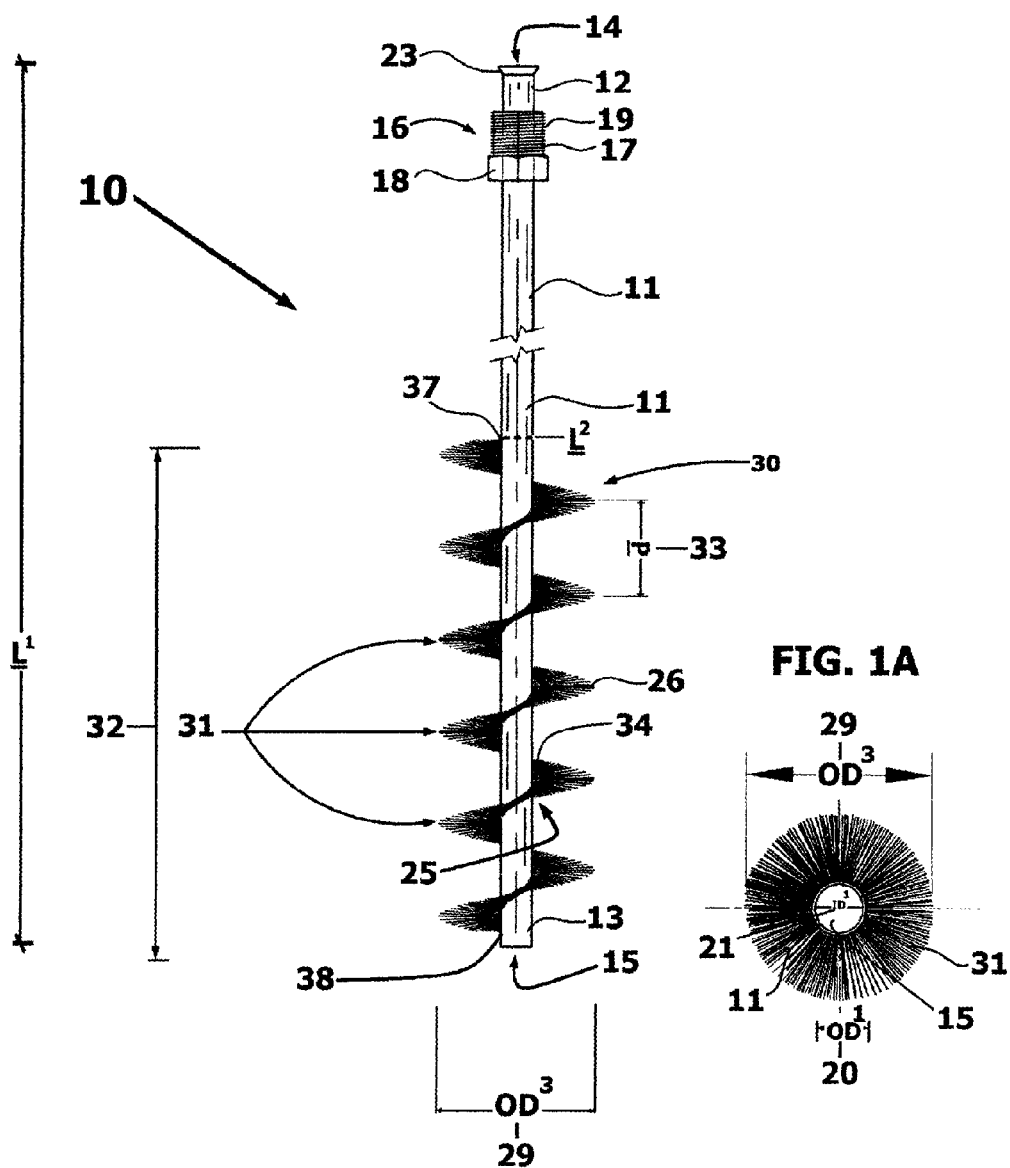
FIG. 1 shows a perspective view of the flash vortex brush device according to a preferred embodiment of the present invention showing the tubular shaft, coil cleaning brush, and connector element.

Chart 1—List of plurality of coil cleaning brush outer diameter ($OD^3$) 29 in relation to inner diameters ($ID^3$) 46 of intended borehole to be cleaned. Also, shown is length "$L^1$" of coil cleaning brush; outer diameter ($OD^1$) 20 tubular shaft.

DICTIONARY

It must be noted that, as used in this specification and the appended claims the following: the singular forms "a," "an" and "the" include plural referents unless the content clearly dictates otherwise. Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The term "comprising", which is synonymous with "including," "containing," or "characterized by," is inclusive or open-ended and does not exclude additional, unrecited elements or method steps.

Flare nut—is synonymous with break line nut.

Into—is synonymous with onto, with.

Propriety Anchor—can comprise anchors, wedge anchors, driven anchors, screwed in wedge anchors, anchor rods, threaded rods, threaded sleeve, screwed in anchors, driven anchors, reinforcing iron, bolts, dowels, steel bars, concrete reinforcing bars, to be bonded to boreholes by epoxy or catalyst cements. Anchors already bonded into boreholes are included.

Operator—person operating the flash vortex brush

NUMERALS

10—Flash Vortex Brush Device
11—Tubular shaft
12—First end of tubular shaft
13—Second end of tubular shaft
14—Defined open inlet
15—Defined open outlet
16—Threaded flare nut [¼ inch pipe or tube×straight thread]
17—First end of flare nut-male connector end of break line nut
18—Second end of flare nut-hex nut end of flare nut
19—Threads on Male connector end of flare nut
20—Outer diameter of tubular shaft [$OD^1$]
21—Inner diameter of tubular shaft [$ID^1$]
22—Scored marks on tubular shaft
23—Flared edge at first end of tubular shaft
24—Through space of Flare Nut
25—Keyway path for flow
26—Radial ends of bristle
27—Base ends of bristle
29—Outer diameter ($OD^3$) of the coil cleaning brush after affixed to tubular shaft
30—Coil cleaning brush
31—Bristles
32—Brush face
33—Pitch
34—Holding channel for bristles
35—Outer diameter coil cleaning brush sleeve [$OD^2$]
36—Inner diameter coil cleaning brush sleeve [$ID^2$]
37—First end of coil cleaning brush
38—Second end of coil cleaning brush
40—Coil cleaning brush sleeve
41—First side wall of holding channel
42—Second side wall of holding channel
43—Flat bottom of holding channel
44—Concrete
45—Concrete borehole
46—Borehole inner diameter [$ID^3$]
47—Borehole bottom
48—Borehole side wall
48a—Borehole side wall
49—Excavated water, residue, dust, debris, small particles from borehole
50—Pre-existing Water Nozzle
51—Pre-existing connection element of pre-existing water nozzle
52—Modified standard hose cap-threaded-Drill and tap for bushing
53—First element, a threaded end cap, of modified standard hose cap-threaded
53a—Threads on end cap, interior 54—Second element, a hole, tapped in modified standard hose cap mates
55—Reducer bushing nut pipe size ⅛×¼ inches [intended for use with water nozzle]
56—Reducer bushing nut male connector end-threaded [intended for use with water nozzle]
57—Reducer bushing nut hex nut female connector end-threaded [intended for use with water nozzle]
58—Threads on male connector end of reducer bushing [intended for use with water nozzle]
59—Threads on internal female hex nut of reducer bushing [intended for use with water nozzle]
60—Pre-existing air nozzle
61—Pre-existing connection element of pre-existing air nozzle
62—Reducer bushing nut-pipe size ⅛×¼ inch [intended for use with air Nozzle]
63—Reducer bushing nut male connector end-threaded [intended for use with air Nozzle]
64—Reducer nut hex nut female connector end-threaded [intended for use with air Nozzle]
65—Pre-existing water hose
66—Through space reducer bushing [intended for use with air nozzle]
67—Threads on male end of reducer bushing [intended for use with air nozzle]
68—Pre-existing air hose
69—Threads in internal portion of hex nut end of reducer bushing nut [intended for use with air nozzle]
70—Tubular Extension Shaft
70 $a$—tubular shaft extension segment
71$a$—First defined open end of extension segment
72$a$—Second defined open end of extension segment
73 $a$—First flared end of extension segment
74 $a$—Second flared end of extension segment
75 $a$—First threaded flare nut on extension segment
76 $a$—Male connector end of first flare nut adapter on extension segment
77$a$—Hex nut end of first flare nut adapter on extension segment
78 $a$—Threads on first flared end nut of extension segment
75 $a^2$—Second threaded flare nut on extension segment
76 $a^2$—Male connector end of second flare nut adapter on first extension segment
77 $a^2$—Hex nut end of second flare nut adapter on extension segment
78 $a^2$—Threads on second flared end nut of extension segment
70 $b$—Second tubular shaft extension segment
71 $b$—First defined open end of extension second segment
72 $b$—Second defined open end of extension second segment
73 $b$—First flared end of extension second segment
74 $b$—Second flared end of extension second segment
75 $b$—First threaded flare nut on extension second segment
76 $b$—male connector end of first flare nut adapter on extension second segment
77 $b$—Hex nut end of first flare nut adapter on extension second segment
78 $b$—Threads on first flared end nut of extension second segment
75 $b^2$—Second threaded flare nut on extension second segment
76 $b^2$—Male connector end of second flare nut adapter on extension second segment
77 $b^2$—Hex nut end of second flare nut adapter on extension second segment
78 $b^2$—Threads on second flared end nut of extension second segment
79—Pre-existing water valve
80—Excavated particles, residue, dust, debris, small particles from borehole
81—Borehole channel
82—Through space in flare nut
83—Retaining wire on coil brush sleeve
90—Union coupling nut
91—Opening in union coupling nut
91$a$—First end of union opening
91$b$—Second end of union opening
92—Cylinder body of union coupling nut
93—Threads interior in union coupling nut
94—Through space connecting first open end and second open end of union coupling nut

DETAILED DESCRIPTION

With reference now to the drawings, and in particular FIGS. 1 through 8 thereof, the principles and concepts of the flash vortex brush apparatus and method will be described. The flash vortex brush device generally designated by the reference number 10 will be described.

Figure 2:
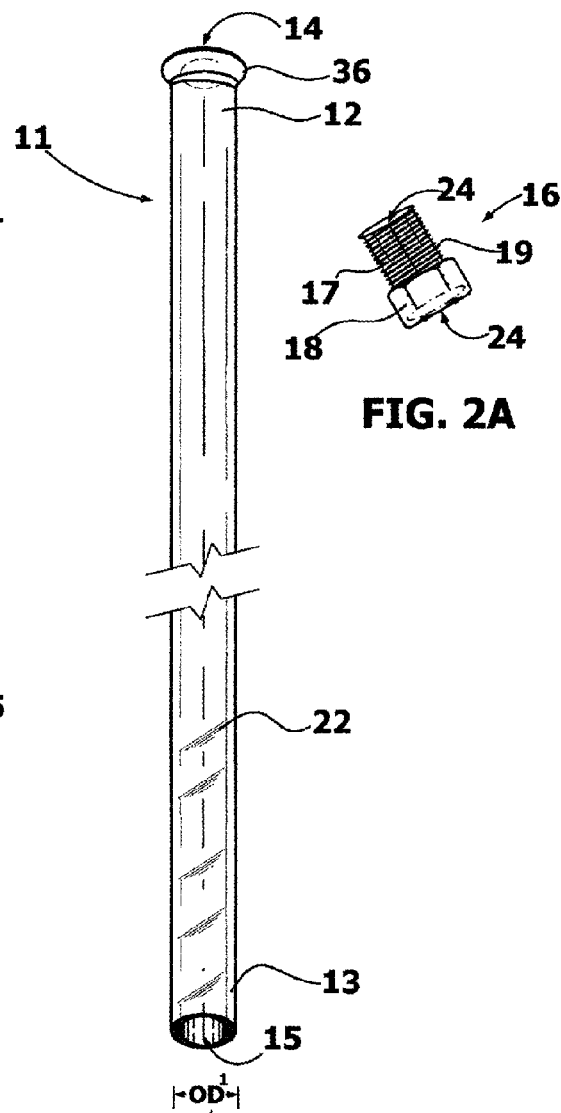
Figure 2A:
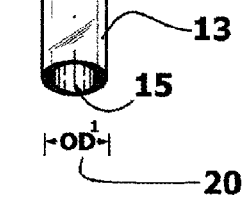
Figure 4:
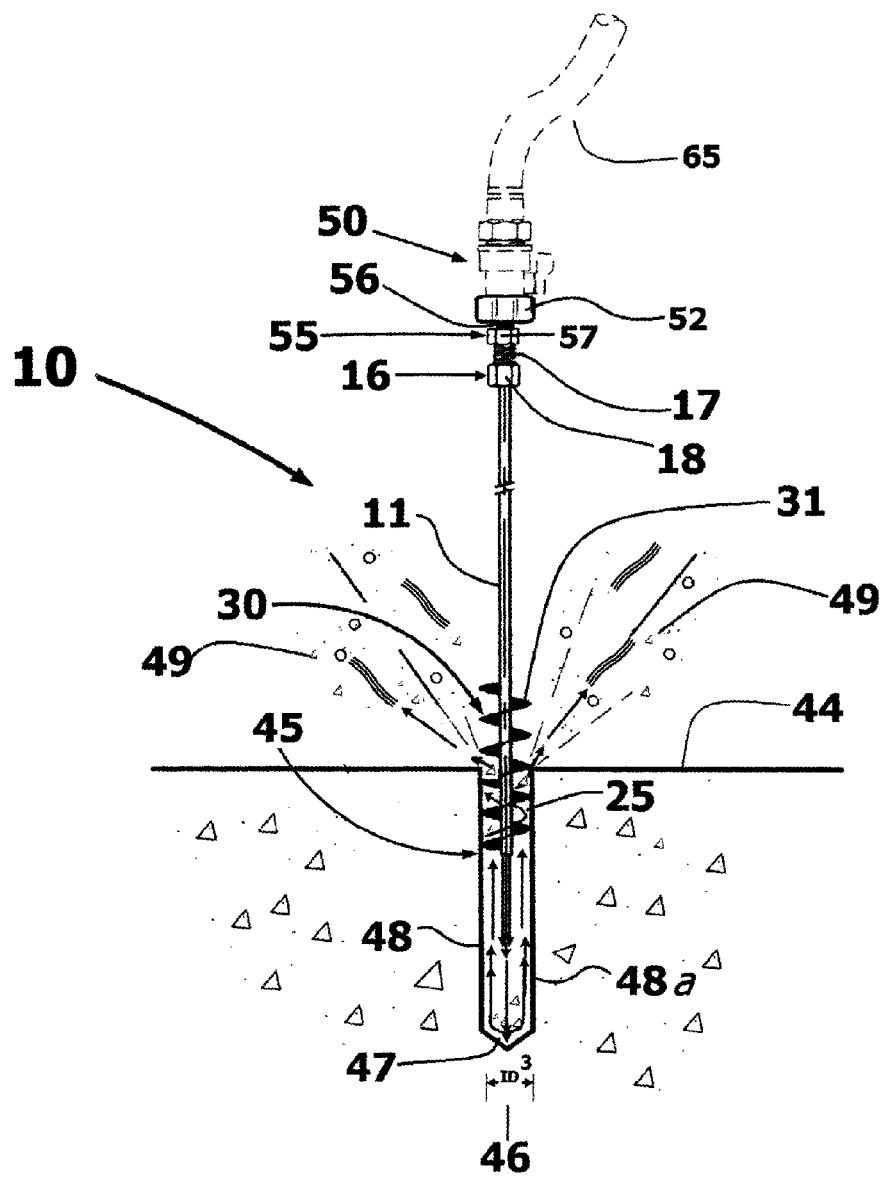
FIG. 4 is a perspective view of the flash vortex brush device according to an embodiment of the present invention, in use, with a pre-existing water nozzle.

Referring to FIGS. 1 and 2 the flash vortex brush device 10 comprises a rigid straight hollow tubular shaft 11 defining a through passage; tubular shaft 11 including a connector element 16 thereon; and a coil cleaning brush 30. The flash vortex brush 10, in use, referring ahead to FIGS. 4 and 6, and described in more detail below, can be readily coupled to pre-existing cleaning nozzles, for example, a pre-existing water nozzle 50 of a type known in the art attached to water hose 65 delivering a powerful laminar jet-stream of water, as illustrated in FIG. 4; and a pre-existing air nozzle 60 of a type known in the art attached to air hose 68, delivering at least approximately 80 to 120 psi of a powerful laminar jet-stream of compressed air. The rigid straight hollow tubular shaft 11 having a first flared end 12 and a second non-flared end 13 serves as the common core for the varied pre existing cleaning nozzles, for example, a pre-existing water nozzle 50; or a pre-existing air nozzle 60; and the coil cleaning brush 30. Further, as shown in FIGS. 1, 1A and 2 the tubular shaft 11 defines a hollow through passage, having a length $L^1$, and the tubular shaft 11 includes a defined open inlet 14 to the hollow space therein at the first flared end 12 and includes an opposing defined open outlet 15 to the hollow space therein at the second non-flared end; the opposing defined open inlet 14 and defined open outlet 15 are joined by at least approximately 12.00 inches in length of the straight tubular shaft 11, but not limited to. In the disclosed example, as shown to FIGS. 1, 1A and 2, the tubular shaft 11 includes an outside diameter ($OD^1$) 20 and can measure approximately ¼ inch, but not limited to; and the tubular shaft 11 includes an internal diameter ($ID^1$) 21 of the tubular shaft 11 and can measure approximately slightly less than ¼ inch, but not limited to. It is to be realized that the optimum dimensional relationships for the elements of the flash vortex brush device 10, including all traits of the tubular shaft 11 and the coil cleaning brush 30 can include variations in size, materials, shape, which are determined by the variety of solid substrates in which the borehole is drilled and the variety of inner diameters of the boreholes, are deemed readily apparent and obvious to one skilled in the art. To that end, the tubular shaft 11 sizes can include a plurality of outer diameters ($OD^1$) 20 configured in direct relation to the inner diameter of the selected borehole to be cleaned. The tubular shaft 11 outer diameter ($OD^1$) 20 determines the base tubular shaft 11 size and the outer diameter ($OD^3$) 29 of the permanently affixed coil cleaning brush 30, as described in detail below. As shown in FIGS. 1 and 2, the first end 12 of the tubular shaft 11 includes a flared edge 23 which provides a holding means or stopping means for the slidably inserted connector element 16, a threaded flare nut 16 which is positioned proximate to the flared end 12 of the tubular shaft 11 of the flash vortex brush device 10. The flare nut 16 provides an attaching means to removably attach the flash vortex brush device 10 to the selected cleaning nozzle. In the disclosed example, as shown in FIG. 1 and more particularly in FIG. 2A the flare nut 16 includes a threaded male connector end 17 and a hex nut end 18 and a through space 24 therein. The flare nut 16 is slidably inserted on the tubular shaft 11 so that the first male connector end 17 extends beyond the first flared end 12 and the second hex nut end 18 is hold at the flared edge 23 of the flared end 12 of the tubular shaft 11. In this manner, the flared nut 16 and can easily be threadably coupled to the varied pre-existing connection elements of pre-existing cleaning nozzles, couplers, unions, and the like, providing for a universally versatile flash vortex brush device 10. The tubular shaft 11 onto which the coil cleaning brush 30 will be mounted can be made of steel, stainless steel, metal, copper, steel, platinum, radium, polyvinyl chloride or other durable materials suitable for the applications provided by the present invention.

Figure 3:
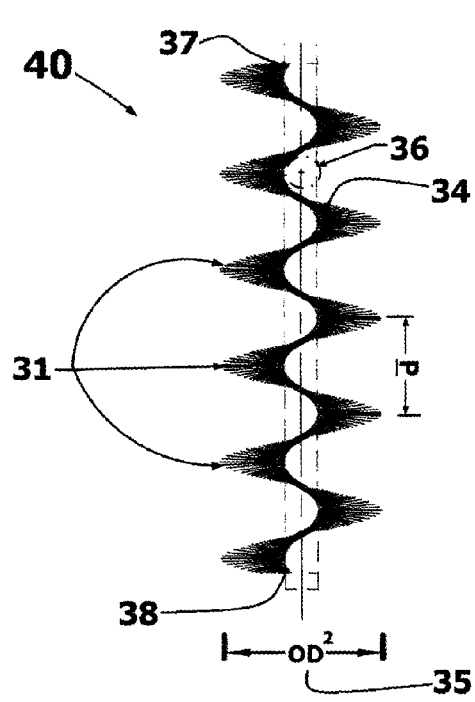
Figure 3A:
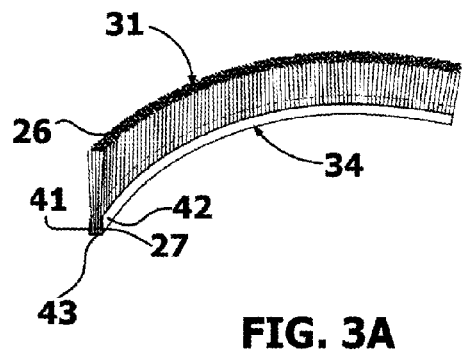

Referring to FIG. 1 the flash vortex brush device 10 includes a coil cleaning brush 30. The coil cleaning brush 30 includes an open wound brush head 32 substantially helical in shape; a holding channel 34 and bristles 31 therein, bristles 31 each having a radial end 26 and a base end 27. As shown in FIG. 1 and more particularly as shown in FIGS. 3 and 3A the coil cleaning brush 30 preferably includes a U-shaped flexible flat back holding channel 34 securing a plurality of bristles 31 the entire length of the holding channel 34 therein. As shown in FIG. 1 the coil cleaning brush 30 is permanently affixed proximate to the second non-flared end 13 of the tubular shaft 11 having a brush face 32 length "$L^2$" open wound convoluting the tubular shaft 11 of pitch "P" 33 to form a brush head 30 having a substantially helix in shape coil and so as, also, to form a generally helical keyway path 25 through in the coil cleaning brush 30 being substantially free of bristles for flow. In the disclosed example, as shown in FIG. 1, the second end 38 of the coil cleaning brush 30 extends from the second non-flared end 13 of the tubular shaft 11 of the flash vortex brush device 10 wound convoluting the tubular shaft 11 to end point of length "$L^2$" to form a coil brush face 32 having a length "$L^2$" approximately 4.00 inches of a pitch "P" 33 approximately 0.75 inches, but not limited to, to form the substantially helix in shape coil cleaning brush 30 and so as, also, to form a generally helical keyway path 25 throughin the coil cleaning brush 30 being substantially free of bristles 31 for flow. Referring to FIG. 1 and FIG. 1A the coil cleaning brush 30 has an outer diameter ($OD^3$) 29. In one exemplary embodiment, the outer diameter ($OD^3$) 29 of the coil cleaning brush 30 is approximately 1.00 inch, but not limited to. The outer diameter ($OD^3$) 29 of the coil cleaning brush 30 can be configured directly proportional to the inner diameter ($ID^3$) 46 of the selected borehole 45 to be cleaned, such that a plurality of flash vortex brush devices 10 can be provided wherein each individual coil cleaning brush 30 affixed upon the tubular shaft 11, as described above. As shown in Chart 1 the coil cleaning brushes can be provided in outer diameters ($OD^3$) 29 comprising of approximately ⅝ inch, ¾ inch, approximately 1.00 inch, approximately 1¼ inch, approximately 1½ inch, approximately 1¾ inch, approximately 2.00 inches, approximately 2¼ inches, approximately 2½ inches, approximately 2¾ inches, and approximately 3.00 inches. Further, any custom size outer diameter ($OD^3$) 29 coil cleaning brush 30 as needed or desired can be configured in direct relation to the inner diameter ($ID^3$) 46 of the selected borehole 45 to be cleaned, such that the coil cleaning brush 30 includes an outer diameter ($OD^3$) 29 slightly less than or equal to the inner diameter ($ID^3$) 46 of the selected borehole 45 to be cleaned. More particularly, as shown in Chart 1 flash vortex brushes outer diameters ($OD^3$) 29 range from approximately ⅝ inch, ¾ inch to approximately 3.00 inches but not limited to, while brush face 32 lengths range from approximately 4.00 inches to approximately 6.00 inches. Tubular shaft 11 outer diameters 29 can be provided in outer diameters 29 of approximately ⅝ inch ¼ inch, but not limited to, and any customized outer diameters needed or desired. Tubular shaft 11 lengths $L^1$ can be provided in lengths at least approximately 12.00 inches, to include approximately 18.00 inches, but not limited to, and any customized length needed or desired corresponding to the depth of the borehole to be cleaned.

CHART 1

| Length of Coil Cleaning Brush 30 | Tubular Shaft 11 Outer Diameter ($OD^1$) 20 | Coil Cleaning Brush 30 Outer Diameter ($OD^3$) 29 | Intended Borehole To Be Cleaned Inner Diameter ($ID^3$) 46 |
|---|---|---|---|
| 4.00 inches | ¼ inch | ⅝ inch | ½ inch-⅝ inch |
| 4.00 inches | ¼ inch | ¾ inch | ⅝ inch-¾ inch |
| 4.00 inches | ¼ inch | 1.00 inch | ⅞ inch-1.00 inch |
| 4.00 inches | ¼ inch | 1¼ inches | 1⅛ inches-1¼ inches |
| 4.00 inches | ¼ inch | 1½ inches | 1⅜ inches-1½ inches |
| 4.00 inches | ¼ inch | 1¾ inches | 1⅝ inches-1¾ inches |
| 4.00 inches | ¼ inch | 2.00 inches | 1⅞ inches-2.00 inches |
| 4.00 inches | ¼ inch | 2¼ inches | 2⅛ inches-2½ inches |
| 4.00 inches | ¼ inch | 2½ inches | 2⅜ inches-2½ inches |
| 4.00 inches | ¼ inch | 2¾ inches | 2⅝ inches-2¾ inches |
| 4.00 inches | ¼ inch | 3.00 inches | 2⅞ inches-3.00 inches |

Again, referring to Chart 1, a plurality of embodiments of the flash vortex brush 10 intended for use in cleaning inner channels of a plurality of selected boreholes are disclosed wherein each individual tubular shaft 11 of the plurality tubular shafts 11 is dimensioned having an outer diameter ($OD^1$) 20 of ¼ inch, and length $L^1$ ($L^1$ not shown in Chart 1) dimensioned from the first flared end to the second non-flared end, $L^1$ at least 12.00 inches, preferably of approximately 18.00 inches, for each individual tubular shaft 11 of the applied embodiments, for clarity, and a plurality of coil cleaning brushes 30 each individual coil cleaning brush 30 affixed to the tubular shaft 11 in the exemplary embodiment wherein each coil cleaning brush 30 having an individual second end 38 of the coil cleaning brush 30 extends from each individual second non-flared end 13 of each of the flash vortex brush device 10 wound convoluting each of the individual tubular shaft 11 to end point of length "$L^2$" to form each individual flash vortex brush 10 each having an individual coil brush face 32 having a length "L" approximately 4.00 inches of a pitch "P" 33 approximately 0.75 inches to form each of the individual substantially helix in shape coil cleaning brushes 30 and so as, also, to form the generally helical keyway paths 25 throughin each individual coil cleaning brush 30 being substantially free of bristles 31 for flow, and further each individual flash vortex brush 10 having each individual coil cleaning brush 30 including an individual outer diameter ($OD^3$) 29 preferred for use to clean the intended selected borehole 45.

Thus, as described in Chart 1 a flash vortex brush device 10 including a coil cleaning brush 30 having an outer diameter ($OD^3$) 29 of approximately ⅝ inch would preferably be used to clean a selected borehole 45 having an inner diameter ($ID^3$) 46 of approximately ½ inch-⅝ inch; a flash vortex brush device 10 including a coil cleaning brush 30 having an outer diameter ($OD^3$) 29 of approximately 34 inch would preferably be used to clean a selected borehole 45 having an inner diameter ($ID^3$) 46 of approximately ⅝ inch-¾ inch; a flash vortex brush device 10 including a coil cleaning brush 30 having an outer diameter ($OD^3$) 29 of approximately 1.00 inch would preferably be used to clean a borehole 45 having an inner diameter ($ID^3$) 46 of approximately ⅞ inch-1.00 inch; a flash vortex brush device 10 including a coil cleaning brush 30 having an outer diameter ($OD^3$) 29 of approximately 1¼ inches would preferably be used to clean a borehole 45 having an inner diameter ($ID^3$) 46 of approximately 1⅛ inches-¼ inches; a flash vortex brush device 10 including a coil cleaning brush 30 having an outer diameter ($OD^3$) 29 of approximately 1½ inches would preferably be used to clean a borehole 46 having an inner diameter ($ID^3$) 46 of approximately 1⅜ inches 1½ inches; a flash vortex brush device 10 including a coil cleaning brush 30 having an outer diameter ($OD^3$) 29 of approximately 1¾ inches would preferably be used to clean a borehole 45 having an inner diameter ($ID^3$) 46 of approximately 1⅝ inches-1¾ inches; a flash vortex brush device 10 including a coil cleaning brush 30 having an outer diameter ($OD^3$) 29 of approximately 2.00 inches would preferably be used to clean a borehole 45 having an inner diameter ($ID^3$) 46 of approximately 1⅞ inches-2 inches; a flash vortex brush device 10 including a coil cleaning brush 30 having an outer diameter ($OD^3$) 29 of approximately 2¼ inches would preferably be used to clean a borehole 45 having an inner diameter ($ID^3$) 46 of approximately 2⅛ inches 2¼ inches; a flash vortex brush device 10 including a coil cleaning brush 30 having an outer diameter ($OD^3$) 29 of approximately 2½ inches would preferably be used to clean a borehole 45 having an inner diameter ($ID^3$) 46 of approximately 2⅜ inches-2½ inches; a flash vortex brush device 10 including a coil cleaning brush 30 having an outer diameter ($OD^3$) 29 of approximately 2¾ inches would preferably be used to clean a borehole 45 having an inner diameter ($ID^3$) 46 of approximately 2⅝ inches-2¾ inches; a flash vortex brush device 10 including a coil cleaning brush 30 having an outer diameter ($OD^3$) 29 of approximately 3.00 inches would preferably be used to clean a borehole 45 having an inner diameter ($ID^3$) 46 of approximately 2⅞ inches-3.00 inches. It is noteworthy, that when the outer diameter ($OD^3$) 29 of the coil cleaning brush 30 exceeds approximately 3.00 inches than the outer diameter ($OD^1$) of the tubular shaft is configured by an increase of approximately ⅛ inch per approximately 1.00 inch increase of outer diameter ($OD^3$) 29 of the coil cleaning brush 30. Brush face 32 lengths range from approximately 4.00 inches to approximately 6.00 inches, but not limited to. As is apparent to one skilled in the art, customized smaller and larger coil cleaning brushes 30 of varied sizes and bristles 31 can be specified and manufactured to correspond to operational needs presented by the dimensions of the selected boreholes to be cleaned.

In the disclosed exemplary embodiment, the plurality of bristles 31 may preferably comprise stiff nylon, but not limited to, to aid, when in use, with reference to FIGS. 4 and 6, as described in more detail below, scraping residue from the interior surfaces of the channel of the borehole 45. The stiff nylon bristles 31 provide durability and corrosion protection. The bristles 31 are stiff to provide superior scraping action, but supple enough to prevent breakage upon contact with the surface of the borehole walls 48 and 48 a. Bristles 31 can be manufactured using synthetics including, but not limited to, nylon, stiff nylon, multiple polymer designations including 6.6, 6.10, 6.12 heat stabilized abrasive impregnated, metal detectable, static control and conductive, polyester, polypropylene, PTFE (Teflon); wire including stainless steel, carbon steel, bronze, brass; animal hair including but not limited to horsehair, hog bristle, goat hair, camel hair, sable hair; vegetable fibers including Tampico, Palmyra, Bassine, Union Fiber, African Bass, and include anti-static capability. In another embodiment, the coil cleaning brush 30 may include any combination of bristles 31, for example, stiff nylon and metal, or stiff nylon and polyester, and the like. The bristles 31 are preferably made using stiff nylon with a density defined by the radial ends 26 of the bristles 31 of approximately 0.001 to 0.035 inch, preferably approximately 0.006 inch, but not limited to. However, one of ordinary skill in the art will realize that the bristle 31 diameter may be changed to create either stiffer or more flexible bristles 31; the thicker the filament of stiff nylon, the stiffer the bristles 31 will be. Thus, the bristle 31 density can be configured so as to vary the stiffness of the coil cleaning brush 30 depending on the anticipated use with selected boreholes 45. One of ordinary skill in the art will realize that the bristle 31 density will have an effect on the effectiveness of the flash vortex brush device 10. Noteworthy, longer bristles 31 will deform more easily but will provide a deep channel helical keyway path 25 which to evacuate debris; shorter bristles 31 will be more rigid and will provide more effective cleaning, but having a correspondingly shallower channel helical keyway path 25 within the borehole 45.

To facilitate manufacture and replacement, the coil cleaning brush 30 used in constructing the flash vortex brush device 10, according to the exemplary disclosed embodiment of the present invention, may be provided initially in the form of a pre-formed coil cleaning brush sleeve 40 shown in FIG. 3 and is indicated at 40, and a cut out segment of the coil cleaning brush sleeve 40 is shown in FIG. 3A for illustrative purposes. The pre-formed coil cleaning brush sleeve 40 is open wound in helical convolutions as shown in FIG. 3 having an outer diameter ($OD^2$) 35 and having a resilient inner diameter ($ID^2$) 36 slightly less than the outer diameter ($OD^1$) 20 of the tubular shaft 11 so that upon installation the coil cleaning brush sleeve 40 slides snugly around the tubular shaft 11 as shown in FIG. 1.

Figure 3B:
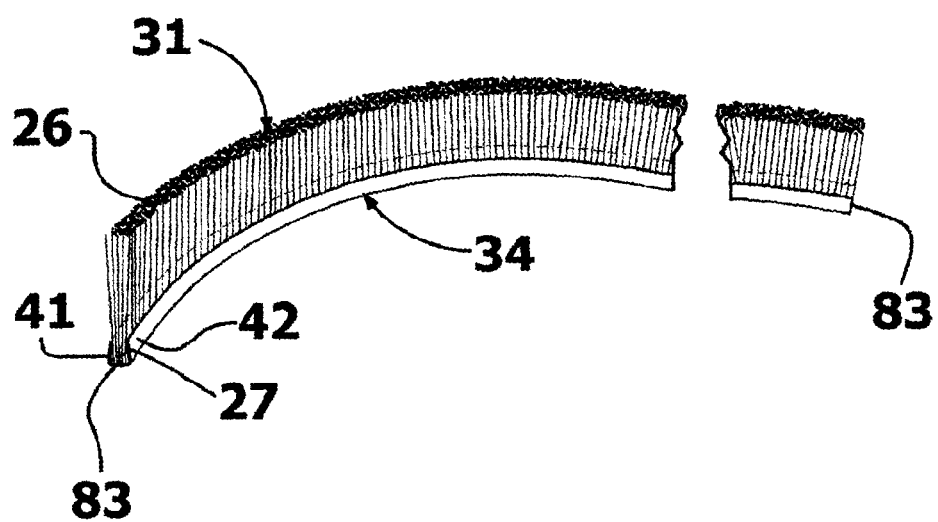
FIG. 3B is a cut-out view of another embodiment of the present invention showing a cut-out of the coil cleaning brush.

As seen more closely in FIG. 3A a cut out segment of the holding channel 34 includes a substantially U-shaped flat back holding channel 34 including two vertically aligned side walls 41 and 42 joined by a horizontally aligned flat bottom base 43 extending for a length "$L^2$", or approximately 4.00 inches, but not limited to. The two sides 41 and 42 are approximately 0.23 inch-0.61 inch range in height and approximately 0.045 inch thickness; the flat bottom base 43 is approximately 0.23 inch 0.50 inch range in width. The holding channel 34 can be manufactured using malleable: metal, steel, stainless steel, brass, plastic, polymeric substrates. As shown in FIG. 3A the holding channel 34 secures the plurality of bristles 31 vertically aligned with their radial ends 26 projecting upward and base ends 27 disposed in the metal holding channel 34 secured by compression. By securing the bristles 31 in this manner, the bristles 31 are less likely to break free and to dislodge from the coil cleaning brush 30 during use. In another embodiment, as shown in FIG. 3B a cut out, for illustrative purposes, shows the coil cleaning brush sleeve 40 having a first end 38 and second end 37, and the holding channel 34 retains "U" shaped bristles 31 vertically aligned with their arcuate base ends 27 disposed in the coiled metal channel 34 secured by a retaining wire 83, having the bristle radial ends 26 extending outward. The ends of the retaining wire 83 extends beyond the adjacent ends of the metal holding channel 34 so that the retaining wire 83 may abet the anchoring of the coil cleaning brush sleeve 40 to the tubular shaft 11. Accordingly, by securing the bristles 31 in this manner, the bristles 31 are less likely to break free and to dislodge from the coil cleaning brush 30 during use.

The coil cleaning brush sleeve 40 can be permanently mounted and affixed convoluting the external surface of the tubular shaft 11 to form the coil cleaning brush 30 with the use of adhesives, for example, with the use of thin layer of fluid adhesives, for example, JB Weld, or can be permanently affixed by the use of clips, J-bolts, tapered locking collars, flanges, compression, wires, or welded, and the like. In the disclosed example, as shown in FIG. 1 the coil cleaning brush sleeve 40 is mounted onto the tubular shaft 11, and more particularly in FIG. 2 the tubular shaft which has been scored 22 to facilitate bonding of the holding channel 34 to the tubular shaft 11 when using fluid adhesives, for example, JB weld.

Method of Use

Figure 5:
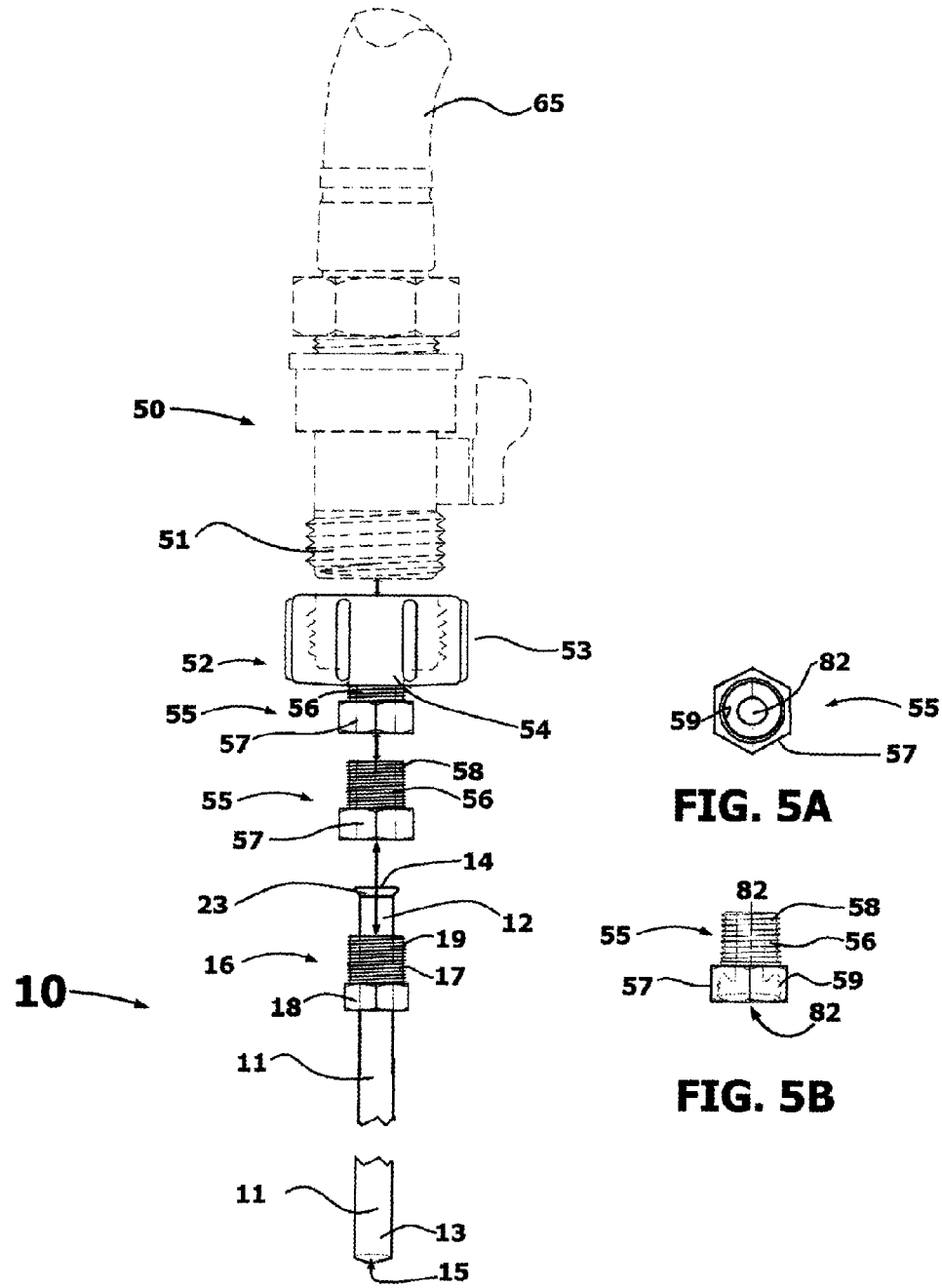

In the following disclosed exemplary embodiments, procedures are disclosed to clean a concrete borehole 45 with the flash vortex brush device 10. However, the method steps are applicable to virtually any type of borehole 45, including a solid substrate, for example, masonry boreholes, grout boreholes, granite boreholes, limestone boreholes, and the like. In one exemplary embodiment, referring to FIGS. 4, 5, 5A and 5B the flash vortex brush 10 is shown in use with a pre-existing water nozzle 50 and includes a method comprising the steps of providing an existing open concrete borehole 45 having a channel inner diameter ($ID^3$) 46 and depth with surrounding walls 48 and 48 *a* therein bound by a closed typically angled or conical bottom surface 47, which has adhered residues of the drilling dust, debris, adhering fine-particle solids, adhering-solid particles, small rocks, and the like, that must be detached and evacuated from the concrete borehole 45. The method further includes providing a flash vortex device 10 having a coil cleaning brush 30 including an outer brush diameter ($OD^3$) 29 selected for the intended borehole 45 having an inner diameter ($ID^3$) 46 to be cleaned. The method for cleaning further includes the step of providing a cleaning nozzle, for example, in the disclosed example, as shown in FIGS. 4 and 5 a pre-existing water nozzle 50 having a pre-existing connection element 51; the pre-existing water nozzle 50 attached to a pre-existing water hose 68 source, and is described in the method below. The use of a pre-existing water nozzle 50 to provide a focused laminar jet-stream of water at rapid velocity would be recommended to clean boreholes that are damp or contain a volume of water, or drill mud.

In another disclosed exemplary embodiment of a method of use of the flash vortex brush device 10, as shown in FIGS. 6,7,7A and 7B the method includes the steps of providing an existing open concrete borehole 45 having a channel inner diameter ($ID^3$) and depth with surrounding walls 48 and 48 *a* therein bound by a closed typically angled or conical bottom surface 47 which has adhered residues of the drilling dust, debris, adhering fine-particle solids, adhering-solid particles, small rocks, and the like, that must be detached and evacuated from the concrete borehole 45. The method further includes providing a flash vortex device 10 having a coil cleaning brush 30 including an outer brush diameter ($OD^3$) 29 selected for the intended borehole 45 having an inner diameter ($ID^3$) 46 to be cleaned. The method for cleaning further includes the step of providing a cleaning nozzle, for example, in the disclosed example, as shown in FIGS. 6, 7, 7A and 7B a pre-existing air nozzle 60 having a pre-existing connection element 61, the pre-existing air nozzle 60 attached to a pre-existing air 68 hose source. The a pre-existing air nozzle 60 attached to an air hose 68 source delivering at least 80-120 psi compressed air is preferred. The pressure required may also increase with the outer diameter ($OD^3$) 29 size of the coil cleaning brush 30 and depth of the concrete 44 borehole 45 to be cleaned. The use of a pre-existing air nozzle 60 to provide a focused laminar jet-stream of compressed air at 80-120 psi is recommended to clean boreholes 45 where the residue, debris, attached small particles, are in a dry state.

The pre-existing water nozzle 50; or in the alternative, the pre-existing air nozzle 60 efficiently and reliably work contemporaneously with the flash vortex brush device 10 while removably affixed to the same core provided by the straight tubular shaft 11, and thereby reduce the amount of steps to clean the concrete borehole 44 by performing two steps of cleaning into one flash vortex brush device 10, the blow step and the brush step. To that end the borehole 45 can be cleaned combining two steps including the blowing step, of delivering laminar jet-stream of high velocity of water, as shown by arrows in FIG. 4 into the borehole 45 channel 81 brushing and the brushing step including the scraping action of the coil cleaning brush 30 bristles 31 of the flash vortex brush device 30; or in the alternative exemplary method, the combining of the two steps, the blowing step including of delivering laminar jet-stream of compressed air, as shown by arrows in FIG. 6 and the brushing step including the scraping action of the coil cleaning brush 30 bristles 31 of the flash vortex brush device 10. The pre-existing water nozzle 50; or the pre-existing air nozzle 60 each individually removably attached to flash vortex brush device 10, directly or via a coupling element, work rapidly and efficiently, so that the debris and residue scraped and detached from the inner channel 81 cement 44 borehole 45 wall surfaces 48 and 48 *a* and bottom surfaces 47, does not redeposit itself; it is rapidly and efficiently evacuated from the depths of the inner channel 81 of the selected cement 44 borehole 45 and exits entrained with the pressurized air, or pressurized water, depending upon the cleaning nozzle 50 or 60 used, such that, the flash vortex brush device 10 and method is able to provide superior cleaning of boreholes 45 in less than one quarter of the time it takes to clean boreholes 45 under the currently practiced standards, therefore, saving money, time, and labor costs, and to ensure reliable bonding of propriety anchors within the boreholes.

First addressing the use of the pre-existing water nozzle 50, the method as shown in FIGS. 4, 5, 5A and 5B of cleaning the inner channel 81 of a selected cement 44 borehole 45 includes the step of providing a flash vortex brush device 10 comprising a rigid hollow straight tubular shaft 11 defining a through passage, connection element 16, preferably a slidable insertable flare nut of ¼ inch, positioned proximate to the first flared end 12; and a coil cleaning brush 30, coil cleaning brush permanently affixed upon the tubular shaft 11. The length of the straight tubular shaft 11, at least 12.00 inches, preferably 18.00 inches, of the selected flash vortex brush device 10 is sufficient to reach the bottom of the selected borehole 45, and the coil cleaning brush 30 includes a plurality of bristles 31, coil cleaning brush having an outside diameter ($OD^3$) 29 equal to or slightly less than the inner diameter ($ID^3$) 46 of the selected concrete borehole 45. If needed, referring ahead to FIG. 8, a tubular extension shaft 70 may be used removably attached between the flare nut 16 positioned on the flash vortex brush device 10 and the pre-existing connection element 51 of the pre-existing water nozzle 50 via a coupling element 90. Now referring back to FIGS. 1 and 2, the tubular shaft 11 has a first flared end 12 and a second non-flared end 13; the first end 12 includes a defined open inlet 14 and the second end 13 includes a defined open outlet 15 joined by the tubular shaft 11 therebetween; the coil cleaning brush 30 convoluting the outer surface of the tubular shaft 11 wound proximate to the second end 13 of the tubular shaft 11 having a brush face 32 having at least 5 coils for a continuous length "$L^2$" mark on the tubular shaft 11 approximately at least approximately 4.00 inches of pitch "P" 33 approximately 0.75 inch, but not limited, to form the substantially helical in shape coil cleaning brush 30 brush head 30 having a substantially helix in shape coil and so as, also, to form a generally helical keyway path 25 throughin the coil cleaning brush 30 being substantially free of bristles for water flow.

The method of cleaning the cement 44 borehole 45 referring now to FIGS. 4 and 5 including the steps of wherein the flash vortex brush device 10 is removably attached to a pre-existing connection element 51 on a pre-existing water nozzle 50 attached to a pre-existing water hose 65 source, of a type known in the art, to provide a source of pressurized jet-stream of water, as indicated by arrows in FIG. 4 blown into the depths of the inner channel 81 of the concrete borehole 45 capable to reach the extended depths of the bottom surfaces 47 and borehole walls 48 and 48a. In the disclosed example, as illustrated in FIGS. 4 and 5, and FIGS. 5A and 5B, the next steps require providing a pre-existing coupling means 55, preferably a pre-existing reducer bushing 55 female pipe size ⅛×¼ inch, as known to those in the art; and providing a modified standard hose cap 52. The pre-existing reducer bushing 55 in an exemplary embodiment of the present invention can include a reducer bushing-female FNPT pipe size ⅛×¼ inch having a threaded first end 56 and opposing threaded second end 57; and a through space 82 therebetween, the first end 56 is a threaded male connector end 56; the second end 57 is threaded female hex nut end 57 joined by the through space 82 therebetween. The modified standard hose cap 52 includes a first connecting end 53, a threaded end cap element 53; and an opposing second connecting end 54, a threaded tapped hole 54. The hex nut end 57 of the reducer bushing 55 includes female threads 59 adapted to mate with the male threads 19 of the male connector end 17 of the flare nut 16. The next step requires positioning the reducer bushing 55 between the threaded flare nut 16 and the modified standard hose cap 52, and inserting the male connector end 17 of the flare nut 16 into the mateable female hex nut end 57 of the reducer bushing 55 and subsequently, tightening and securely threadably removably attaching together the male connector end 17 of the flare nut 16 of the tubular shaft to the hex nut end 57 of the reducer bushing 55. Next, the male connector end 56 of the reducer bushing 55 includes male threads 58 adapted to mate with female threads 53a on the interior tapped hole 54 of the modified standard hose cap 52. The next step of the method requires inserting the threaded male connector end 56 of the reducer bushing 55 into the mateable threaded female tapped hole 54 of the modified standard hose cap 52, and subsequently, tightening and securely threadalby removably attaching together the male connector end 56 of the reducer bushing 55 to the tapped hole 54 of the modified standard hose cap 52.

In turn, the first element of the modified standard hose cap 52 is a female threaded end cap 53 adapted to mate with a male thread 53a on the pre-existing water nozzle connection element 51 of the pre-existing water nozzle 50. The next step requires, positioning the female threaded end cap 53 proximate to the male threaded pre-existing connection element 51 of the pre-existing water nozzle 50 and inserting the female threaded end cap 53 onto the pre-existing connection element 51 of the pre-existing water nozzle 50 and subsequently tightening and securely threadably removably attaching the threaded end cap 53 of the modified standard hose cap 52 to the pre-existing connection portion 51 of the pre-existing water nozzle. Ultimately, as shown in FIGS. 4 and 5 the flash vortex brush 10 and the pre-existing water nozzle 50 are securely threadably removably attached together.

Referring to FIGS. 4 and 5 when the pre-existing water nozzle 50 is threadably removably attached to the flare nut 16 proximate to the first end 12 of the tubular shaft 11 a handle is formed as a holding means for the operator of the flash vortex brush 10. In addition, the defined open inlet 14, as shown in FIG. 5, of the flash vortex brush device 10 provides a means for receiving water into the hollow tubular shaft 11 to be propelled and circulated throughin the channel 81 of the cement 44 borehole 45; and the defined open outlet 15 provides a means for blowing water into the inner channel 81 of the borehole 45.

The flash vortex brush device 10 is ready to use in the next step of the method of cleaning the borehole 45. The operator cleans the selected cement 44 borehole 45 by manually inserting and moving the flash vortex brush 10 into the channel 81 of the cement 44 borehole 45 leading with the coil cleaning brush 11 permanently affixed to the of the tubular shaft 11. Next step combines two steps into one step provided by the flash vortex brush 10 and requires, impelling the jet-stream of pressurized water through the hollow tubular shaft 11 and blowing the jet-stream of water, as indicated by arrows in FIG. 4, into the channel of the cement 44 borehole 45 typically by activating a pre-existing trigger of the pre-existing water nozzle 50 impelling a focused jet-stream of pressurized water, indicated by arrows, as shown in FIG. 4, into the hollow tubular shaft 11 to be propelled and circulated in the channel 81 of the cement 44 borehole 45 and contemporaneously manually brushing the inner channel 81 of the borehole 45 moving the flash vortex brush device 10 through the length of the interior channel 81 of the borehole 45 in a repeating movements such that the plurality of bristles 31 of the coil cleaning brush 30 contacts the interior cement walls 48 and 48a scraping the adhering residues, debris, dust, mud, adhering fine-particle solids, rocks, stones, the dislodged residue material falling to the bottom surfaces 47 of the cement 44 borehole 45. In the position shown in FIG. 4 the flash vortex brush device 10 has been run to the interior of the borehole 45 channel 81, and can be further inserted within the channel 81 proximate to the borehole bottom 47 surfaces with the coil cleaning brush 30 and jet stream of pressurized water, as indicated by arrows in FIG. 4, having dislodged debris and residue, and other materials adhered to the inner walls 48 and 48a of the cement 44 borehole 45. The impelled focused laminar jet-stream of pressurized water is blown through the defined open outlet 15 of the flash vortex brush device 10 where the laminar water stream is powerfully blown downwards into the channel 81 of the cement 44 borehole 45 reaching and contacting the cement 44 borehole 45 wall surfaces 48 and 48 *a* and bottom surfaces 47 and concomitant with the movement of the coil cleaning brush 30 causing a powerful vortex of water entrained with deposits, debris, detached fine-particle solids, small rocks, small stones, dust, residue 49 thus scraped to be forced upwards through the annuli between the flash vortex brush device 10 and the borehole walls 48 and 48 *a* and through the keyway path 25 throughin the coil cleaning brush 30, therefore, transporting and evacuating said debris 49 from the interior of the cement borehole 45 with the expelled pressurized water out to the environment.

The next step in the cleaning method includes the operator manually drawing the flash vortex brush 10 out of the cement borehole 45. To ensure complete removal of the debris and residue material 49, the flash vortex brush 10 is raised and lowered and brushed along the boreholes walls 48 and 48 *a* repeated times before being drawn out of the borehole 45, while continuing to blow the jet-stream of powerful pressurized water into the channel 81 of the cement 44 borehole 45. The next step requires the operator to repeat the above described steps of manually inserting the flash vortex brush 10 into the channel 81 of the concrete 44 borehole 45 and blowing the laminar impelled jet-stream of water into the channel 81 of the borehole 45 contemporaneous with brushing the inner borehole 45 walls 48 and 48*a* followed by manually drawing the flash vortex brush device 10 out of the cement 44 borehole 45. In the position shown in FIG. 4 the flash vortex brush device 10 has been inserted into the channel 81 of the borehole 45, and can be further inserted within the channel 81 proximate to the borehole bottom 47 surfaces with the coil cleaning brush 30 and powerful jet-stream of water, as indicated by arrows, having dislodged debris and residue, and other materials adhered to the inner walls 48 and 48*a* of the cement 44 borehole 45. The impelled jet-stream of water, as indicated by arrows, in FIG. 4, is blown through the defined open outlet 15 of the flash vortex brush device 10 where the water is powerfully impelled downwards into the channel 81 of the cement 44 borehole 45 able to reach and contact the borehole wall surfaces 48 and 48*a* bottom surfaces 47 and concomitant with the brushing of the coil cleaning brush 30 provides a powerful vortex of water which entrains deposits, debris, detached fine-particle solids, small rocks, small stones, dust, residue 49 thus scraped and collected on the bottom to be forcibly propelled upwards through the helical keyway path 25 of the coil cleaning brush 30 and the annuli between the flash vortex brush 10 and the borehole walls 48 and 48*a*, thereby, transporting and evacuating said debris 49 from the interior channel 81 of the cement 44 borehole 45 with the pressurized jet-stream of water out to the environment.

The steps of manually inserting the flash vortex brush device 10 and manually drawing out of the flash vortex brush device 10 and the brushing of the inner borehole walls 48 and 48*a* contemporaneously with the blowing of a powerful focused laminar jet stream of water, as indicated by arrows in FIG. 4 is repeated over again, and again, until the cement 44 borehole 45 is thoroughly cleaned. A drilled concrete 44 borehole 45 is efficiently and effectively cleaned, when upon follow-up inspection, using a pre-existing nozzle 60 attached to a pre-existing air source hose 68 threadably coupled to a hollow straight tubular shaft 11 at least 12.00 inches in length, preferably 18.00 inches, without a coiled cleaning brush 30, as shown in FIG. 2 is inserted into the newly cleaned cement 44 borehole 45 such that when a pressurized laminar jet-stream of air is blown down into the channel 81 reaching the bottom 47 of the cement 44 borehole 45, no visible dust or fine-particle solids, or residue 49 exits the newly cleaned concrete 44 borehole 45.

As disclosed in the exemplary embodiment, the contemporaneous blowing of pressurized water and brushing of the flash vortex brush device 10 "in and out" of the borehole 45 channel 81 provides for high cleaning performance of boreholes 45 in cement 44 by increased detachment of residues of the drilling dust, debris, adhering fine-particle solids, adhering-solid particles, small rocks, and residues 49 and increased removal of debris and residues from the boreholes 45. The blowing of the jet-stream of pressurized water into the channel 81 of the borehole 45 concomitant with the brushing of the inner surfaces of the borehole 45 channel 81 is capable of reaching the sidewalls 48 and 48*a* and reaching extended depths contacting the bottom floor surface 47 of the borehole channel to ensure superior cleaning to the interior bottom surface 47 of the borehole 45 channel 81, thereby the flash vortex brush device 10 provides for optimal bond of anchors with the cement 44 of the borehole 45.

By using this novel invention, the debris 49 left from the coring or drilling process is substantially completely evacuated from the concrete 44 borehole 45 by combining the blowing step and the brushing step, taking from 5 to 10 seconds in holes 1½ inches and smaller, using minimally amounts of water. Larger boreholes 45 are cleaned by the same method but do take additional time and water pressure, in relation to the borehole 45 size. The clean borehole 45 allows the propriety anchor to work, efficiently and reliably, at its designed holding power. The flash vortex brush device 10 provides a device and method to clean boreholes 45 which comprises combining two steps, currently practiced in cleaning boreholes, when cleaning a wet or damp borehole: (1) the blowing step; and (2) the brushing step into one flash vortex brush device 10 and method. Time, labor, costs, are decreased while borehole 45 cleaning efficiency and effectiveness is increased. The flash vortex brush device 10 and method can be adjusted to work with any propriety borehole 45 size and type; and the flash vortex brush device 10 and method can be adapted to be used with various cleaning nozzles.

The pre-existing water nozzle 50 can easily be removed and a pre-existing air nozzle 60 can be threadably coupled to the flash vortex brush device 10. Referring now to FIGS. 6, 7, and 7A, there is shown another embodiment of the flash vortex brush device 10 indicated generally by reference numeral 10.

The first step in the method of cleaning the inner channel 81 of a selected cement 44 borehole 45 with a flash vortex brush device 10 in use with a pre-existing air nozzle 60 includes providing a flash vortex brush device 10 comprising a rigid hollow straight tubular shaft 11 defining a through passage, connection element 16, preferably a slidable insertable flare nut of ¼ inch, positioned proximate to the first flared end 12; and a coil cleaning brush 30, coil cleaning brush permanently affixed upon the tubular shaft 11. The length of the straight tubular shaft 11, length at least 12.00 inches, preferably 18.00 inches, of the selected flash vortex brush device 10 is sufficient to reach the bottom of the selected borehole 45, preferably approximately 18.00 inches, and the coil cleaning brush 30 includes a plurality of bristles 31, coil cleaning brush having an outside diameter ($OD^3$) 29 equal to or slightly less than the inner diameter ($ID^3$) 46 of the selected concrete borehole 45. If needed, referring ahead to FIG. 8, a tubular extension shaft 70 may be used removably attached between the flare nut 16 positioned on the flash vortex brush device 10 and the pre-existing connection element 61 of the pre-existing air nozzle 60, via a coupling element 90. Now referring back to FIGS. 1 and 2, the tubular shaft 11 has a first flared end 12 and a second non-flared end 13; the first end 12 includes a defined open inlet 14 and the second end 13 includes a defined open outlet 15 joined by the tubular shaft 11 therebetween; the coil cleaning brush 30 convoluting the outer surface of the tubular shaft 11 wound proximate to the second end 13 of the tubular shaft 11 having a brush face 32 having at least 5 coils for a continuous length "$L^2$" mark on the tubular shaft 11 approximately at least approximately 4.00 inches of pitch "P" 33 approximately 0.75 inch, but not limited, to form the substantially helical in shape coil cleaning brush 30 brush head 30 having a substantially helix in shape coil and so as, also, to form a generally helical keyway path 25 throughin the coil cleaning brush 30 being substantially free of bristles for air flow.

The method of cleaning further includes the steps of removably attaching the flash vortex brush device 10 to the pre-existing connection element 61 of a pre-existing air nozzle device 60. In the disclosed example, as illustrated in FIGS. 4 and 5, and FIGS. 5A and 5B, the next steps require providing a pre-existing coupling means 62, preferably a pre-existing reducer bushing 62 female pipe size ⅛×¼ inch, as known to those in the art. The pre-existing reducer bushing 62 in an exemplary embodiment of the present invention can include a reducer bushing-female FNPT pipe size ⅛×¼ inch having a threaded first end 63 and opposing threaded second end 64; and a through space 66 therebetween, the first end 63 is a threaded male connector end 63; the second end 64 is threaded female hex nut end 64 joined by the through space 66 therebetween. In the disclosed example, as illustrated in FIGS. 6, 7,7A, and 7B, the flare nut 16 positioned proximate to the first flare end 12 of the tubular shaft 11 of the flash vortex brush 10 may be removably attached with a pre-existing coupling element 62, preferably a pre-existing reducer bushing 62, as known to those in the art. As shown in FIGS. 6, 7, 7A and 7B this step of the method of cleaning the inner channel of the selected cement 44 borehole 45 using a pre-existing air nozzle 60 having a pre-existing connection portion 61 includes providing a pre-existing coupling element, 62, preferably a pre-existing reducer bushing 62 pipe size ⅛×¼ inch, as known to those in the art. As shown, more particularly, in FIGS. 7A and 7B the reducer bushing 62 hex nut end 64 includes female threads 69 adapted to mate with the male threads 19 of the male connector end 17 of the flare nut 16 positioned proximate to the first end 12 of the tubular shaft 11 on the flash vortex brush 10. The reducer 62 male connector end 63 of the reducer bushing 62 includes a male thread 67 adapted to mate with a female thread [not shown] on the pre-existing air nozzle adapter end 61. The next step in the cleaning method includes positioning the reducer bushing 62 between the flare nut 16 positioned on the tubular shaft 11 of the flash vortex brush 10 and the pre-existing connection element 61 of the pre-existing air nozzle 60. The next step requires inserting the male connector end 17 of the flex nut 16 into the female hex nut end 64 of the reducer bushing 62, and, subsequently, tightening and securely threadably attaching the flare nut 16 with the reducer bushing 62 at the hex nut end 64. The next step requires inserting the male connector end 63 of the reducer bushing 62 into the female pre-existing connection end 61 of the pre-existing air nozzle 60, and subsequently, tightening and securely threadably attaching the reducer bushing 62 at the male connector end 63 with the pre-existing connection element 61 of the pre-existing air nozzle. Ultimately, the pre-existing air nozzle 60 and the flash vortex brush 10 are securely removably threadably attached together.

When the pre-existing cleaning air nozzle 60 is assembled to the flare nut 16 proximate to the first end 12 of the tubular shaft 11 *a* handle is formed as a holding means for the operator of the flash vortex brush 10. In addition, the defined open inlet 14, as shown in FIG. 5, of the flash vortex brush device 10 provides a means for receiving air into the hollow tubular shaft 11 to be propelled and circulated throughin the channel 81 of the cement 44 borehole 45; and the defined open outlet 15 provides a means for blowing air into the inner channel 81 of the borehole 45.

The flash vortex brush device 10 is ready to use in the next step of the method of cleaning the borehole 45 using a pre-existing air nozzle 60. The operator cleans the selected cement 44 borehole 45 by manually inserting and moving the flash vortex brush 10 into the channel 81 of the cement borehole 45 leading with the coil cleaning brush 30 affixed to the tubular shaft 11; and blowing an impelled focused laminar jet-stream of compressed air at 80-120 psi, by activating an existing trigger of the air nozzle 60; a trigger as well known in the art.

The flash vortex brush device 10 is ready to use in the next step of the method of cleaning the borehole 45. The operator cleans the selected cement 44 borehole 45 by manually inserting and moving the flash vortex brush 10 into the channel 81 of the cement 44 borehole 45 leading with the coil cleaning brush 11 permanently affixed to the of the tubular shaft 11. Next step combines two steps into one step, the blowing step and the brushing step, provided by the flash vortex brush 10 and requires, impelling the jet-stream of pressurized air through the hollow tubular shaft 11 and blowing the jet-stream of air, as indicated by arrows in FIG. 6, into the channel of the cement 44 borehole 45 typically by activating a pre-existing trigger of the pre-existing air nozzle 60 impelling a focused jet-stream of pressurized air, indicated by arrows, as shown in FIG. 6, into the hollow tubular shaft 11 to be propelled and circulated in the channel 81 of the cement 44 borehole 45 and contemporaneously manually brushing the inner channel 81 of the borehole 45 moving the flash vortex brush device 10 through the length of the interior channel 81 of the borehole 45 in a repeating movements such that the plurality of bristles 31 of the coil cleaning brush 30 contacts the interior cement walls 48 and 48 *a* scraping the adhering residues, debris, dust, mud, adhering fine-particle solids, rocks, stones, the dislodged residue material falling to the bottom surfaces 47 of the cement 44 borehole 45.

Figure 6:
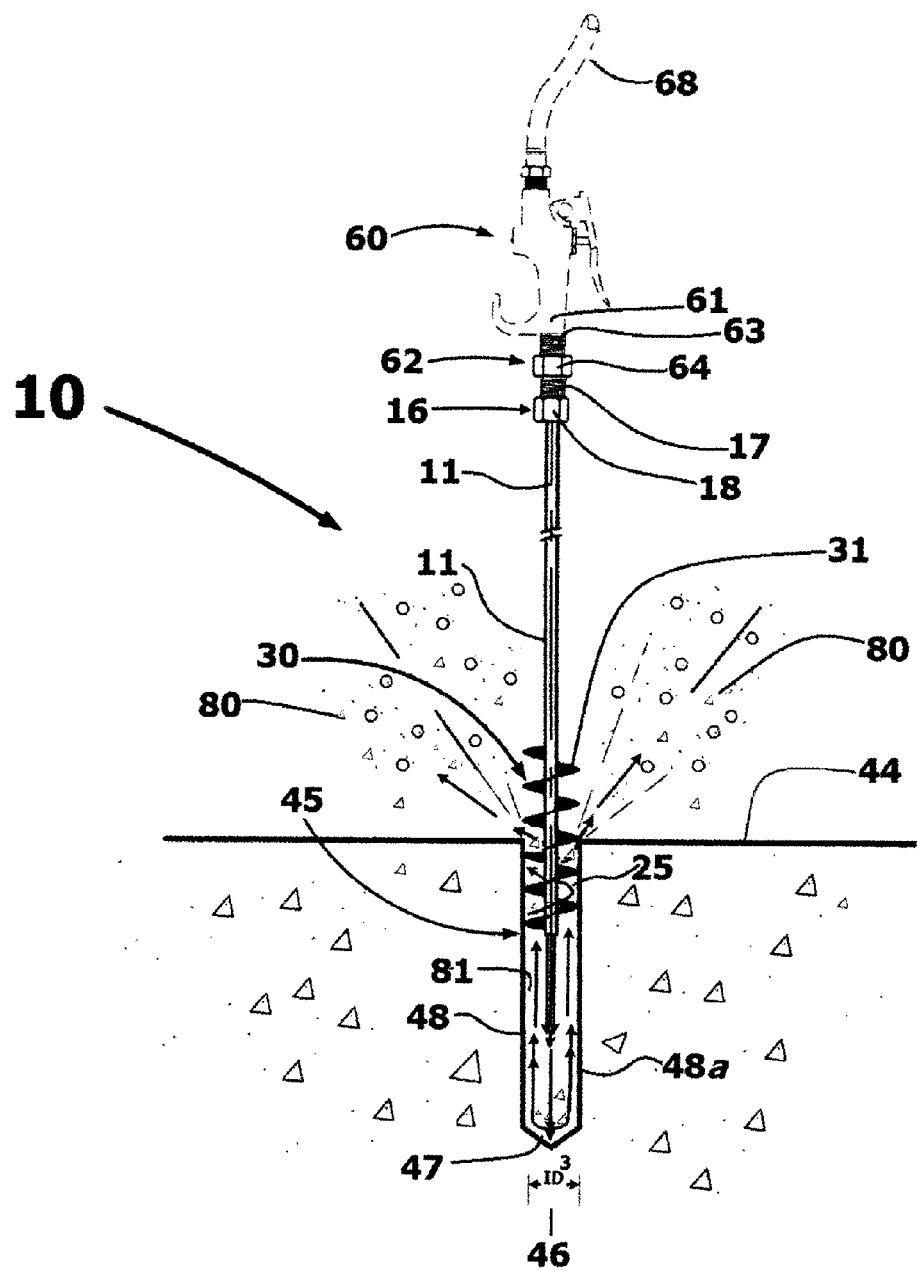
FIG. 6 is a perspective view of the flash vortex brush device according to another embodiment of the present invention, in use, with a pre-existing air nozzle.

In the position shown in FIG. 4 the flash vortex brush device 10 has been run to the interior of the borehole 45 channel 81, and can be further inserted within the channel 81 proximate to the borehole bottom 47 surfaces with the coil cleaning brush 30 and focused laminar jet-stream of compressed air, as indicated by arrows in FIG. 6, having dislodged debris and residue, and other materials adhered to the inner walls 48 and 48*a* of the cement 44 borehole 45. The impelled focused laminar jet-stream of compressed air is blown through the defined open outlet 15 of the flash vortex brush device 10 where the laminar air stream is powerfully blown downwards into the channel 81 of the cement 44 borehole 45 reaching and contacting the cement 44 borehole 45 wall surfaces 48 and 48 *a* and bottom surfaces 47 and concomitant with the movement of the coil cleaning brush 30 causing a powerful vortex of air entrained with deposits, debris, detached fine-particle solids, small rocks, small stones, dust, residue 80 thus scraped to be forced upwards through the annuli between the flash vortex brush device 10 and the borehole walls 48 and 48 *a* and through the keyway path 25 throughin the coil cleaning brush 30, therefore, transporting and evacuating said debris 80 from the interior of the cement borehole 45 with the expelled pressurized air out to the environment.

The next step in the cleaning method includes the operator manually drawing the flash vortex brush 10 out of the cement borehole 45. To ensure complete removal of the debris and residue material 80, the flash vortex brush 10 is raised and lowered and brushed along the boreholes walls 48 and 48 *a* repeated times before being drawn out of the borehole 45, while continuing to blow the jet-stream of powerful compressed air into the channel 81 of the cement 44 borehole 45. The next step requires the operator to repeat the above described steps of manually inserting the flash vortex brush 10 into the channel 81 of the concrete 44 borehole 45 and blowing the laminar impelled jet-stream of air into the channel 81 of the borehole 45 contemporaneous with brushing the inner borehole 45 walls 48 and 48*a* followed by manually drawing the flash vortex brush device 10 out of the cement 44 borehole 45. In the position shown in FIG. 4 the flash vortex brush device 10 has been inserted into the channel 81 of the borehole 45, and can be further inserted within the channel 81 proximate to the borehole bottom 47 surfaces with the coil cleaning brush 30 and powerful jet-stream of air, as indicated by arrows, having dislodged debris and residue, and other materials adhered to the inner walls 48 and 48*a* of the cement 44 borehole 45. The impelled jet-stream of air, as indicated by arrows, in FIG. 6 is blown through the defined open outlet 15 of the flash vortex brush device 10 where the air is powerfully impelled downwards into the channel 81 of the cement 44 borehole 45 able to reach and contact the borehole wall surfaces 48 and 48*a* bottom surfaces 47 and concomitant with the brushing of the coil cleaning brush 30 provides a powerful vortex of air which entrains deposits, debris, detached fine-particle solids, small rocks, small stones, dust, residue 80 thus scraped and collected on the bottom to be forcibly propelled upwards through the helical keyway path 25 of the coil cleaning brush 30 and the annuli between the flash vortex brush 10 and the borehole walls 48 and 48*a*, thereby, transporting and evacuating said debris 80 from the interior channel 81 of the cement 44 borehole 45 with the pressurized jet-stream of air out to the environment.

The steps of manually inserting the flash vortex brush device 10 and manually drawing out of the flash vortex brush device 10 and the brushing of the inner borehole walls 48 and 48*a* contemporaneously with the blowing of a powerful focused laminar jet stream of air, as indicated by arrows in FIG. 4 is repeated over again, and again, until the cement 44 borehole 45 is thoroughly cleaned. A drilled concrete 44 borehole 45 is efficiently and effectively cleaned, when upon follow-up inspection, using a pre-existing nozzle 60 attached to a pre-existing air source hose 68 threadably coupled to a hollow straight tubular shaft 11 at least 12.00 inches in length, preferably 18.00 inches, without a coiled cleaning brush 30, as shown in FIG. 2 is inserted into the newly cleaned cement 44 borehole 45 such that when a pressurized laminar jet-stream of air is blown down into the channel 81 reaching the bottom 47 of the cement 44 borehole 45, no visible dust or fine-particle solids, or residue 80 exits the newly cleaned concrete 44 borehole 45.

As disclosed in the exemplary embodiment, the contemporaneous blowing of pressurized water and brushing of the flash vortex brush device 10 "in and out" of the borehole 45 channel 81 provides for high cleaning performance of boreholes 45 in cement 44 by increased detachment of residues of the drilling dust, debris, adhering fine-particle solids, adhering-solid particles, small rocks, and residues 80 and increased removal of debris and residues 80 from the boreholes 45. The blowing of the powerful jet-stream of compressed air into the channel 81 of the borehole 45 concomitant with the brushing of the inner surfaces of the borehole 45 channel 81 is capable of reaching the sidewalls 48 and 48*a* and reaching extended depths contacting the bottom floor surface 47 of the borehole channel to ensure superior cleaning to the interior bottom surface 47 of the borehole 45 channel 81, thereby the flash vortex brush device 10 provides for optimal bond of anchors with the cement 44 of the borehole 45.

By using this novel invention, the debris 80 left from the coring or drilling process is substantially completely evacuated from the concrete 44 borehole 45 by combining the blowing step and the brushing step, taking from 5 to 10 seconds in holes 1½ inches and smaller, using minimally amounts of air. Larger boreholes 45 are cleaned by the same method but do take additional time and air pressure, in relation to the borehole 45 size. The clean borehole 45 allows the propriety anchor to work, efficiently and reliably, at its designed holding power. The flash vortex brush device 10 provides a device and method to clean boreholes 45 which comprises combining two steps, currently practiced in cleaning boreholes, when cleaning a dry borehole: (1) the blowing step; and (2) the brushing step into one flash vortex brush device 10 and method. Time, labor, costs, are decreased while borehole 45 cleaning efficiency and effectiveness is increased. The flash vortex brush device 10 and method can be adjusted to work with any propriety borehole 45 size and type; and the flash vortex brush device 10 and method can be adapted to be used with various cleaning nozzles.

Figure 8:
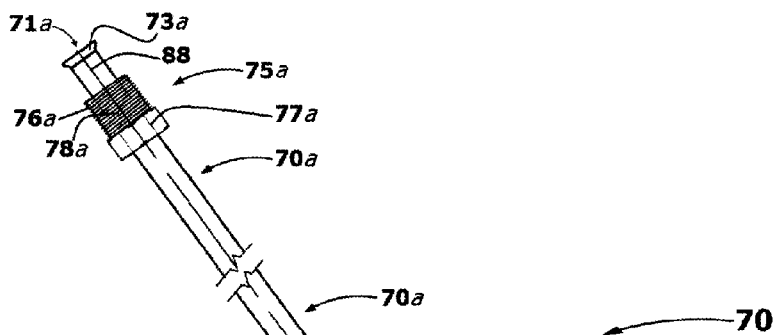
FIG. 8—is a perspective view of an extension shaft segment.
Figure 8A:
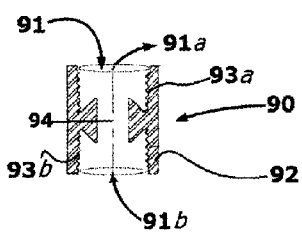
Figure 8B:
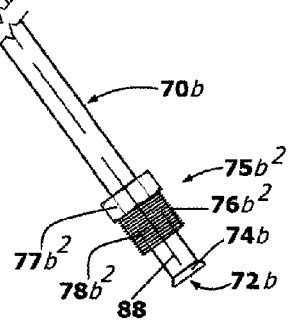

Referring now to FIG. 8 of the drawings, wherein like numerals indicate like elements, another embodiment of the flash vortex brush device 10 is shown. In this embodiment, a rigid hollow tubular shaft extension 70 is shown to be used with the flash vortex brush 10 device used with a pre-existing cleaning nozzle, for example, a pre-existing water nozzle 50, or a pre-existing air nozzle 60, intended to clean existing boreholes 45 having channel 81 depths that require the additional length provided by the shaft extension 70 typically angled or conical bottom surfaces 47 of the borehole 45 and the surrounding borehole walls 48 and 48*a*. In the disclosed embodiment, FIG. 8 shows a plurality of rigid tubular shaft extension 70 segments 70*a* and 70*b* which can be dimensioned at least approximately 18.00 inches, but not limited to, each extension segment 70*a*, 70*b* having first flared ends 73*a* and 73*b* and opposing second flared ends 74*a* and 74*b*; and further including opposing defined open ends 71*a* and 72*a*; and 71*b* and 72*b*, respectively. Each tubular shaft extension 70*a*, 70*b* further includes first threaded flare nuts 75*a* and 75*b* and opposing second threaded flare nuts 75$a^2$ and 75$b^2$. Each of the flared nuts 75 *a*, 75 $a^2$, 75 *b*, 75 $b^2$, includes male connector ends 76 *a*, 76 $a^2$, 76 *b*, 76 $b^2$, respectively, and further includes female hex nut ends 77 *a*, 77 $a^2$, 77 *b*, 77 $b^2$, respectively. Each of the male connector ends 76*a*, 76$a^2$, 76*b*, 76$b^2$ include threads 78*a*, 78$a^2$, 78*b*, 78$b^2$; respectively. The plurality of extension segments 70*a* and 70*b* may be removably attached together, for example, as shown in FIG. 8 by threadably removably attaching each extension segment 70 *a*, 70*b* by means of a coupling means 90, the coupling means 90, preferably a union coupling nut 90, but not limited to. The union coupling nut 90, as more particularly shown in FIGS. 8A and 8B includes a generally cylindrical hex body 92 defining a through space 94, the union coupling nut 90 includes two opposing substantially identical open ends 91*a* and 91*b*. The union 90 open ends 91*a* and 91*h* include interior female threads 93*a* and 93*b* which are universally versatile, can be securely threadably coupled to the mating male threaded flare nuts 75a and 75b, or to second male threaded flare nuts 75a² and 75b² of each of the tubular shaft extensions 70a, 70b. The flare nuts 75 a, 75a², 75b, 75 b² includes exterior male threads 78 a, 78 a², 78 b, 78 b²; respectively, on the male connector ends 76 a, 76 a², 76b, 76 b² that are matable with each of the female threads 93a, 93 b of the union coupler 90 and thereby the two extension segments 70 a and 70 b can be threadably removably attached to each other along the longitudinal axis of the extension 70. The cleaning procedure would then proceed as described above.

The tubular extension 70 can be manufactured using steel, stainless steel, metal, copper, brass, steel, platinum, radium, polyvinyl chloride or other durable materials.

In another embodiment, the union 90 may include any coupling means having an internal through space with locking means mateable to removably attach extensions shaft segments 70a, 70b to each other.

The flash vortex brush 10 may have utility cleaning other solid boreholes 45 or other tubular holes having a channel with a bottom end in solid substrates when the tubular hole cleaning requires application of the blowing of a laminar focused jet-stream of pressurized water concomitant with the brushing action of the coil cleaning brush 30 action of the flash vortex brush device 10; or in the alternative, the cleaning requires application of the blowing of a lamina focused jet-stream of compressed air concomitant with the brushing action of the coil cleaning brush 30 of the flash vortex brush device 10. In one embodiment of the present invention, the flash vortex brush device 10 may be used to clean and disinfect the interior channel 81 and surrounding walls 48 and 48a of an existing borehole 45 wherewith the flash vortex brush device 10 may be utilized to apply protective, dissolution, or disinfecting coatings to the inside channel 81 of the borehole 45 and its surrounding walls 48 and 48a during a cleaning process where an anchor will be bonded by epoxies or catalyst cements. In one example, a mold-inhibiting solution prepared and applied with a water nozzle affixed to the flash vortex brush device may be used.

The flash vortex brush device 10 offers an advantage over present boreholes cleaning methods which require multiple separate cleaning steps. Utilizing the flash vortex brush device of the present invention, provides a device and method including contemporaneous blowing of pounding pressurized water with use with a pre-existing water nozzle 50, or contemporaneous blowing of pounding compressed air with use with a pre-existing air nozzle, and the brushing action of the coiled cleaning brush 30 bristles 31 contacting the borehole walls 48 and 48a Therefore, the flash vortex brush device 10 and method provides for optimal bond of anchors with the cement of the borehole while reducing time, labor, and costs.

It is to be understood that this invention is not limited to particularly exemplified systems or process parameters that may, of course, vary. It is also to be understood that the terminology used is for the purpose of describing particular embodiments of the invention only, and is not intended to limit the scope of the invention in any manner.

While the present invention has been described with reference to a particular preferred embodiment and the accompanying drawings, it will be understood by those skilled in the art that the invention is not limited to the preferred embodiment and that various modifications and the like could be made thereto without departing from the scope of the invention as defined in the following claims.

I claim:
1. A flash vortex brush device intended for use, in cleaning inner circumferential and bottom surfaces of a borehole having an inner diameter ($ID^3$), the flash vortex brush device, comprising of:
a non-perforated rigid straight tubular shaft defining a through passage including a first end having a first opening defining an open inlet and an opposing second end having a second opening defining an open outlet and including a length "$L^1$" being 18.00 inches therebetween, the non-perforated rigid straight tubular shaft having an outer diameter ($OD^1$) being ¼ inch is less than the inner diameter ($ID^3$) of the borehole, the first end including a flared end and the opposing second end including a non-flared end;
a threaded flare nut insertably slidable positioned thereon the flared end;
wherein the threaded flare nut being ¼ inch includes a threaded male connector end and an opposing hex nut end and a through space therethrough, the opposing hex nut end held proximate to the flared end of the non-perforated rigid straight tubular shaft such that the threaded male connector end is extended beyond the flared end of the non-perforated rigid straight tubular shaft;
a coil cleaning brush including a first brush end and a second brush end joined by an open wound coil brush face therebetween, the coil cleaning brush including a plurality of defined bristles each of the defined bristles having a radial side and a base side wherein each of the base sides of the defined bristles are secured by a holding channel juxtaposed to the non-perforated rigid straight tubular shaft;
wherein the coil cleaning brush is permanently affixed with an epoxy to the non-perforated rigid straight tubular shaft at the holding channel having the first brush end permanently affixed proximate to an end point of a length "$L^2$" mark on the non-perforated rigid straight tubular shaft and the second brush end permanently affixed proximate to the non-flared end of the non-perforated rigid straight tubular shaft such that the plurality of the defined bristles extend radially outward from the non-perforated rigid straight tubular shaft and convoluting around the non-perforated rigid straight tubular shaft to form the coil cleaning brush including 5 coils of a length being 4.00 inches and of a pitch "P" being 0.75 inch having an outer diameter ($OD^3$) being ¾ inch and causing the plurality of the defined bristles to form a brushing surface to be in a helical shape including a helical keyway path through the brushing surface being free of the plurality of the defined bristles for flow;
a modified hose cap including a threaded female end cap and a threaded female hole therethrough;
a reducer bushing nut including a threaded reducer bushing nut male connector at a first end and a threaded female hex nut connector at a second end and having a through space therethrough;
wherein the reducer bushing nut being ⅛×¼ inch pipe size is positioned between the threaded male connector end of the threaded flare nut and the modified hose cap; and
wherein the threaded female hex nut connector of the reducer bushing nut is removably threadably attached into the threaded male connector end of the threaded flare nut, and the threaded reducer bushing nut male connector of the reducer bushing nut is removably threadably attached into the threaded female hole of the modified hose cap and the threaded female end cap is removably threadably attached into a threaded male connection element of a water nozzle.

2. The flash vortex brush device of claim 1, wherein the coil cleaning brush is permanently affixed with welding to the non-perforated rigid straight tubular shaft at the holding channel.

3. The flash vortex brush device of claim 1, wherein the non-perforated rigid straight tubular shaft is made with stainless steel.

4. The flash vortex brush device of claim 1, wherein outer diameter ($OD^3$) of the coil cleaning brush is 5/8 inch.

5. The flash vortex brush device of claim 1, wherein outer diameter ($OD^3$) of the coil cleaning brush is 1.00 inch.

6. The flash vortex brush device of claim 1, wherein outer diameter ($OD^3$) of the coil cleaning brush is 1¼ inches.

7. The flash vortex brush device of claim 1, wherein outer diameter ($OD^3$) of the coil cleaning brush is 1½ inches.

8. The flash vortex brush device of claim 1, wherein outer diameter ($OD^3$) of the coil cleaning brush is 1¾ inches.

9. The flash vortex brush device of claim 1, wherein outer diameter ($OD^3$) of the coil cleaning brush is 2.00 inches.

10. The flash vortex brush device of claim 1, wherein outer diameter ($OD^3$) of the coil cleaning brush is 2½ inches.

11. The flash vortex brush device of claim 1, wherein outer diameter ($OD^3$) of the coil cleaning brush is 2¾ inches.

12. The flash vortex brush device of claim 1, wherein outer diameter ($OD^3$) of the coil cleaning brush is 3.00 inches.

13. A flash vortex brush device intended for use in cleaning inner circumferential and bottom surfaces of a borehole having an inner diameter ($ID^3$), the flash vortex brush device, comprising:
   a non-perforated rigid straight tubular shaft defining a through passage including a first end having a first opening defining an open inlet and an opposing second end having a second opening defining an open outlet including a length "$L^1$" of at least 12 inches therebetween and having an outer diameter ($OD^1$) less than the inner diameter ($ID^3$) of the borehole, the first end including a flared end and the opposing second end including a non-flared end;
   a threaded flare nut insertably slidable positioned thereon the flared end;
       wherein the threaded flare nut includes a threaded male connector end and an opposing hex nut end and a through space therethrough, the opposing hex nut end held proximate to the flared end of the non-perforated rigid straight tubular shaft such that the threaded male connector end is extended beyond the flared end of the non-perforated rigid straight tubular shaft;
   a coil cleaning brush including a first brush end and a second brush end joined by an open wound coil brush face therebetween, the coil cleaning brush including a plurality of defined bristles each of the defined bristles having a radial side and a base side wherein each of the base sides of the defined bristles are secured by a holding channel juxtaposed to the non-perforated rigid straight tubular shaft;
   wherein the coil cleaning brush is permanently affixed to the non-perforated rigid straight tubular shaft at the holding channel with the first brush end permanently affixed proximate to an end point of a length "$L^2$" mark on the non-perforated rigid straight tubular shaft and the second brush end permanently affixed proximate to the non-flared end of the non-perforated rigid straight tubular shaft such that the plurality of the defined bristles extend radially outward from the non-perforated rigid straight tubular shaft and convoluting around the non-perforated rigid straight tubular shaft to form the coil cleaning brush including a at least 5 coils of a length of "$L^2$" and of a pitch "P" having an outer diameter ($OD^3$) equal to or slightly less than the inner diameter ($ID^3$) of the borehole and greater than the outer diameter ($OD^1$) of the non-perforated rigid straight tubular shaft, and causing the plurality of the defined bristles to form a brushing surface to be in a helical shape including a helical keyway path through the brushing surface being free of the plurality of the defined bristles for flow;
   a modified hose cap including a threaded female end cap and a threaded female hole therethrough;
   a reducer bushing nut including a threaded reducer bushing nut male connector at a first end and a threaded female hex nut connector at a second end and having a through space therethrough is positioned between the threaded male connector end of the threaded flare nut and the modified hose cap; and
   wherein the threaded female hex nut connector of the reducer bushing nut is removably threadably attached into the threaded male connector end of the threaded flare nut, and the threaded reducer bushing nut male connector of the reducer bushing nut is removably threadably attached into the threaded female hole of the modified hose cap and the threaded female end cap is removably threadably attached into a threaded male connector connection element of a water nozzle.

14. The flash vortex brush device of claim 13, wherein the non-perforated rigid tubular shaft length is 18 inches.

15. The flash vortex brush device of claim 13, wherein the outer diameter ($OD^1$) of the non-perforated rigid straight tubular shaft is ¼ inch.

16. The flash vortex brush device of claim 13, wherein the non-perforated rigid straight tubular shaft is made with stainless steel.

17. The flash vortex brush device of claim 13, wherein the coil cleaning brush is permanently affixed with an epoxy to the non-perforated rigid straight tubular shaft at the holding channel.

18. The flash vortex brush device of claim 13, wherein the coil cleaning brush is permanently affixed with welding to the non-perforated rigid straight tubular shaft at the holding channel.

19. The flash vortex brush device according to claim 13, wherein the coil cleaning brush comprises an outer diameter ($OD^3$) of at least one outer diameter ($OD^3$) selected from the group consisting of 5/8 inch, ¾ inch, 1.00 inch, 1¼ inches, 1½ inches, 1¾ inches, 2.00 inches, 2¼ inches, 2½ inches, and 3.00 inches.

20. The flash vortex brush device according to claim 13, wherein the at least 5 coils of the coil cleaning brush is 4.00 inches measured from the first brush end to the second brush end causing the at least 5 coils to have the pitch "P" to measure 0.75 inch.

21. The flash vortex brush device according to claim 13, wherein the threaded flare nut is ¼ inch.

22. The flash vortex brush device according to claim 13, wherein the reducer bushing nut is a 1/8×¼ inch pipe size.

23. A flash vortex brush device intended in cleaning inner circumferential and bottom surfaces of a borehole having an inner diameter ($ID^3$), the flash vortex brush device, consisting of:
   a non-perforated rigid straight tubular shaft having a length $L^1$ being 18.00 inches defining a through passage including a first end having a first opening defining an open inlet, and an opposing second end defining an open outlet, the non-perforated rigid tubular shaft having an outer diameter ($OD^1$) being ¼ inch which is less than the inner diameter ($ID^3$) of the borehole, the first end having a flared end and the opposing second end having a non-flared end;

a threaded flare nut insertably slidable positioned thereon the flared end, the threaded flare nut being ¼ inch;

wherein the threaded flare nut includes a threaded male connector end and an opposing hex nut end and a through space therethrough, the opposing hex nut end held proximate to the flared end of the non-perforated rigid straight tubular shaft such that the threaded male connector end is extended beyond the flared end of the rigid straight tubular shaft;

a coil cleaning brush including a plurality of defined bristles having a first brush end and a second brush end is permanently affixed to the non-perforated rigid straight tubular shaft at a holding channel having the first brush end permanently affixed proximate to an end point of a length "$L^2$" mark on the non-perforated rigid straight tubular shaft and the second brush end permanently affixed proximate to the non-flared end of the non-perforated rigid straight tubular shaft such that the plurality of the defined bristles extend radially outward from the non-perforated rigid straight tubular shaft and convoluting around the non-perforated rigid straight tubular shaft to form the coil cleaning brush including 5 coils of a length being 4.00 inches and of a pitch "P" being 0.75 inch having an outer diameter ($OD^3$) being ¾ inch which is less than the inner diameter of the borehole and causing the plurality of the defined bristles to form a brushing surface to be in a helical shape including a helical keyway path through the brushing surface being free of the plurality of the defined bristles for flow;

a modified hose cap including a threaded female end cap and a threaded female hole therethrough;

a reducer bushing nut including a threaded reducer bushing nut male connector at a first end and a threaded female hex nut connector at a second end and having a through space therethrough, the reducer bushing nut being a ⅛×¼ inch pipe size is positioned between the threaded male connector end of the threaded flare nut and the modified hose cap and operable to connect the non-perforated rigid straight tubular shaft to a threaded male connection element of a water nozzle;

and wherein the threaded female hex nut connector of the reducer bushing nut is removably threadably attached into the threaded male connector end of the threaded flare nut, and the threaded reducer bushing nut male connector of the reducer bushing nut is removably threadably attached into the threaded female hole of the modified hose cap and the threaded female end cap is removably threadably attached into the threaded male connection element of the water nozzle.

24. The flash vortex brush device of claim 23, wherein the coil cleaning brush comprises an outer diameter ($OD^3$) selected from the group consisting of: ⅝ inch, ¾ inch, 1.00 inch, 1¼ inch, 1½ inches, 1¾ inches, 2.00 inches, 2¼ inches, and 3.00 inches.

25. The flash vortex brush device of claim 23, wherein the coil cleaning brush is permanently affixed to the non-perforated rigid straight tubular shaft at the holding channel with epoxy.

26. The flash vortex brush device of claim 23, wherein the coil cleaning brush is permanently affixed to the non-perforated rigid straight tubular shaft at the holding channel with welding.

27. The flash vortex brush device of claim 23, wherein the non-perforated rigid straight tubular shaft is made with stainless steel.

* * * * *